US006648818B2

(12) United States Patent
Cartier et al.

(10) Patent No.: US 6,648,818 B2
(45) Date of Patent: *Nov. 18, 2003

(54) ARTICULATION MEMBER FOR USE IN A SURGICAL APPARATUS

(75) Inventors: Raymond Cartier, Ville Mont-Royal (CA); Anthony Paolitto, St-Léonard (CA)

(73) Assignee: Coroneo, Inc., Montreal (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/877,046

(22) Filed: Jun. 11, 2001

(65) Prior Publication Data
US 2001/0034473 A1 Oct. 25, 2001

Related U.S. Application Data

(63) Continuation of application No. 09/482,052, filed on Jan. 13, 2000, now Pat. No. 6,273,853, which is a continuation of application No. 08/940,766, filed on Sep. 30, 1997, now Pat. No. 6,102,854.

(51) Int. Cl.[7] .............................................. A61B 17/01
(52) U.S. Cl. ...................................... 600/228; 600/234
(58) Field of Search ................................ 600/201, 226, 600/227, 228, 229, 235, 234

(56) References Cited

U.S. PATENT DOCUMENTS

| 2,670,731 A | 3/1954 | Zoll et al. |
| 3,227,156 A | 1/1966 | Gauthier |
| 3,467,079 A | 9/1969 | James |
| 3,724,449 A | 4/1973 | Gauthier |
| 3,749,088 A | 7/1973 | Gauthier |
| 3,965,890 A | 6/1976 | Gauthier |
| 4,048,987 A | 9/1977 | Hurson |
| 4,151,837 A | 5/1979 | Millard, Jr. et al. |

(List continued on next page.)

FOREIGN PATENT DOCUMENTS

| DE | 297 07 567 U1 | 8/1997 |
| EP | 791330 A2 | 8/1997 |
| SU | 876-119 | 10/1981 |
| WO | WO 96/32882 | 10/1996 |
| WO | WO 96/40354 | 12/1996 |

Primary Examiner—Cary E. O'Connor

(57) ABSTRACT

An articulation member for use in a surgical apparatus is provided. The articulation member includes a fitting for mounting to a support structure, a socket for receiving an arm of a surgical tool and a clamp moveable between a loosened position and a tightened position. In the loosened position the clamp permits movement between the fitting and the support structure, and permits rotation of the socket. In the tightened position, the clamp secures the fitting and the arm relative to the support structure.

47 Claims, 37 Drawing Sheets

U.S. PATENT DOCUMENTS

| | | |
|---|---|---|
| 4,156,424 A | 5/1979 | Burgin |
| 4,300,541 A | 11/1981 | Burgin |
| 4,368,997 A | 1/1983 | Shemtov |
| 4,627,421 A | 12/1986 | Symbas et al. |
| 4,718,151 A | 1/1988 | Le Vahn et al. |
| 4,726,356 A | 2/1988 | Santilli et al. |
| 4,747,394 A | 5/1988 | Watanabe |
| 4,813,401 A | 3/1989 | Grieshaber |
| 4,829,985 A | 5/1989 | Couetil |
| 4,852,552 A | 8/1989 | Chaux |
| 4,865,019 A | 9/1989 | Phillips |
| 4,926,849 A | 5/1990 | Downey |
| 4,932,395 A | 6/1990 | Mehdizadeh |
| 4,949,707 A | 8/1990 | Le Vahn et al. |
| 4,971,038 A | 11/1990 | Farley |
| 4,989,587 A | 2/1991 | Farley |
| 5,025,779 A | 6/1991 | Bugge |
| 5,052,373 A | 10/1991 | Michelson |
| 5,088,472 A | 2/1992 | Fakhrai |
| 5,117,822 A | 6/1992 | Laghi |
| 5,139,498 A | 8/1992 | Astudillo Ley |
| 5,167,223 A | 12/1992 | Koros et al. |
| 5,299,563 A | 4/1994 | Seton |
| 5,363,841 A | 11/1994 | Coker |
| D361,381 S | 8/1995 | Koros et al. |
| 5,503,617 A | 4/1996 | Jako |
| 5,520,610 A | 5/1996 | Giglio et al. |
| 5,571,072 A | 11/1996 | Kronner |
| 5,607,471 A | 3/1997 | Seguin et al. |
| 5,616,117 A | 4/1997 | Dinkler et al. |
| 5,618,260 A | 4/1997 | Caspar et al. |
| 5,792,046 A * | 8/1998 | Dobrovolny ............... 600/234 |
| 5,876,332 A * | 3/1999 | Looney .................... 600/102 |
| 5,888,247 A | 3/1999 | Benetti |
| 5,894,843 A | 4/1999 | Benetti |
| 5,957,835 A | 9/1999 | Anderson et al. |
| 6,283,912 B1 * | 9/2001 | Hu et al. .................. 600/232 |
| 6,322,500 B1 * | 11/2001 | Sikora et al. ............. 600/219 |

* cited by examiner

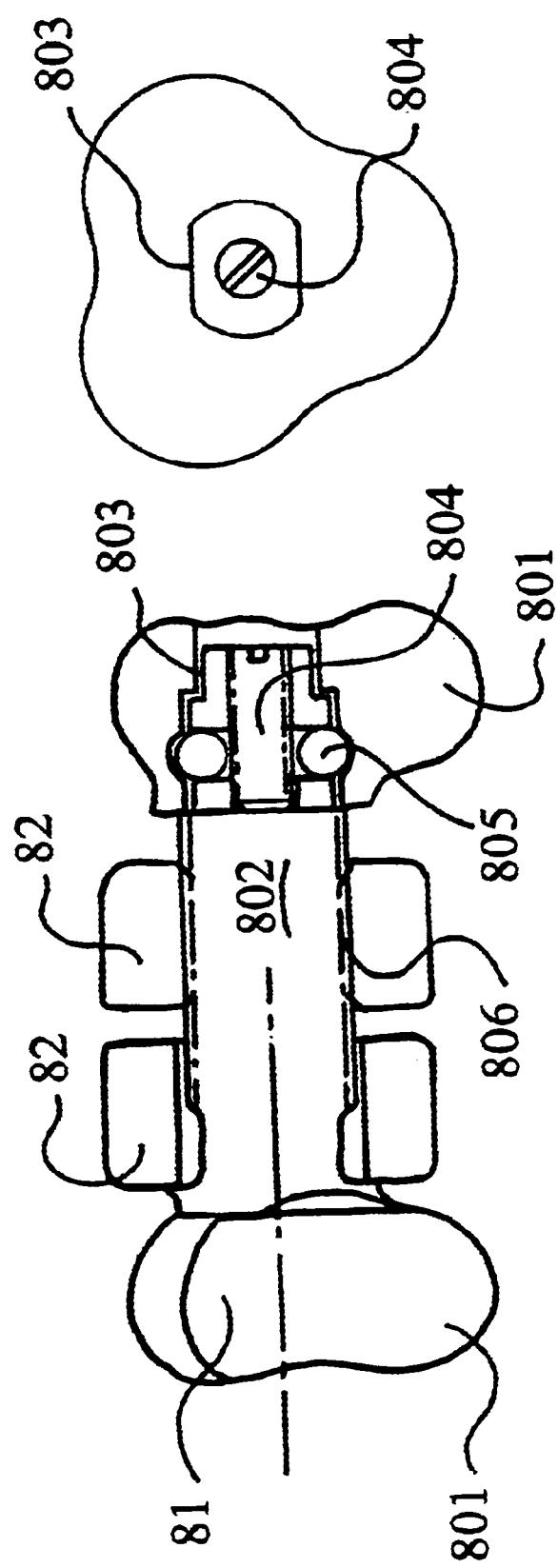

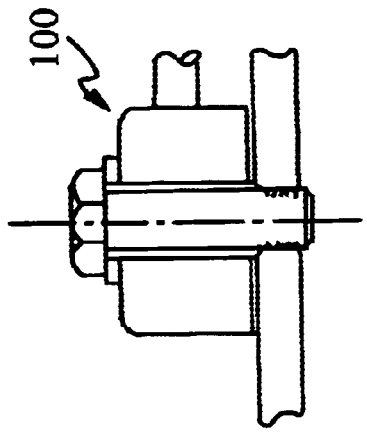
Figure 15C
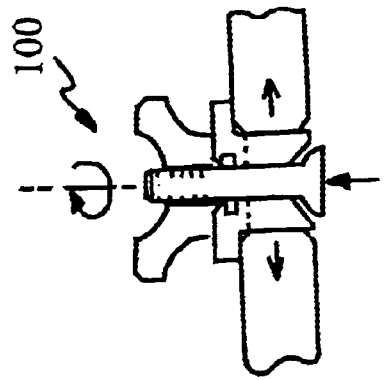
Figure 15F
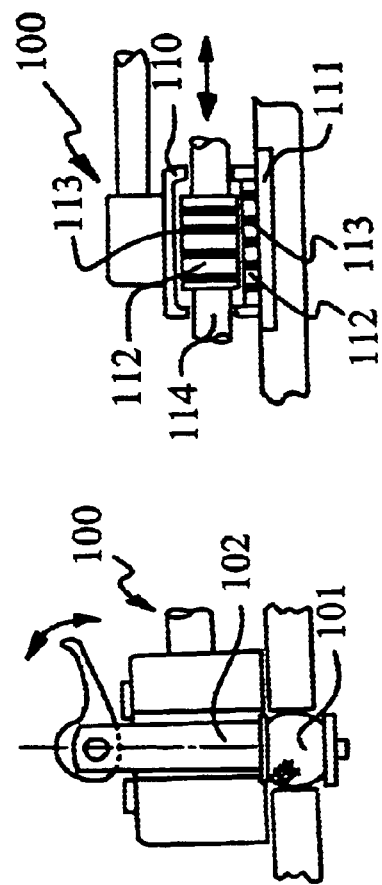
Figure 15B
Figure 15A
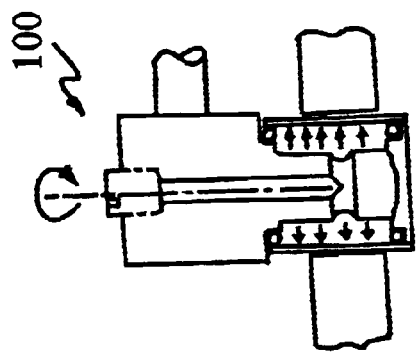
Figure 15E
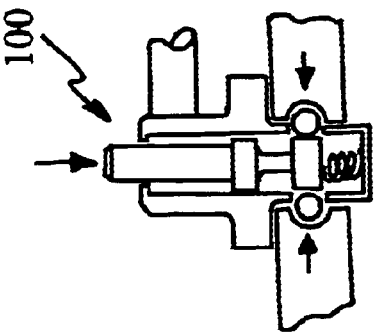
Figure 15D

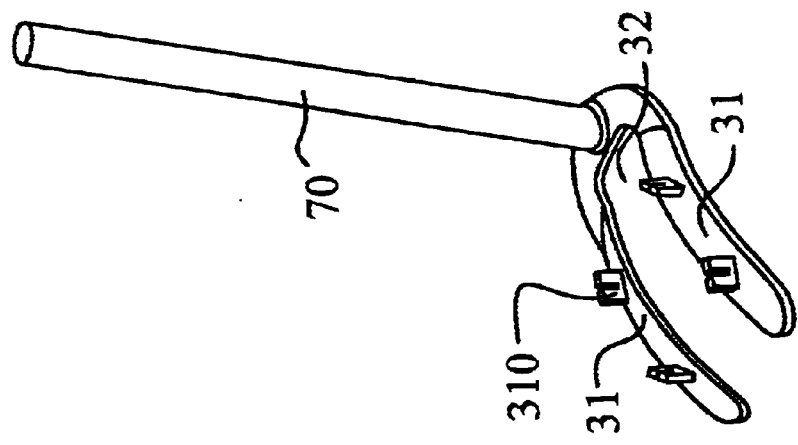
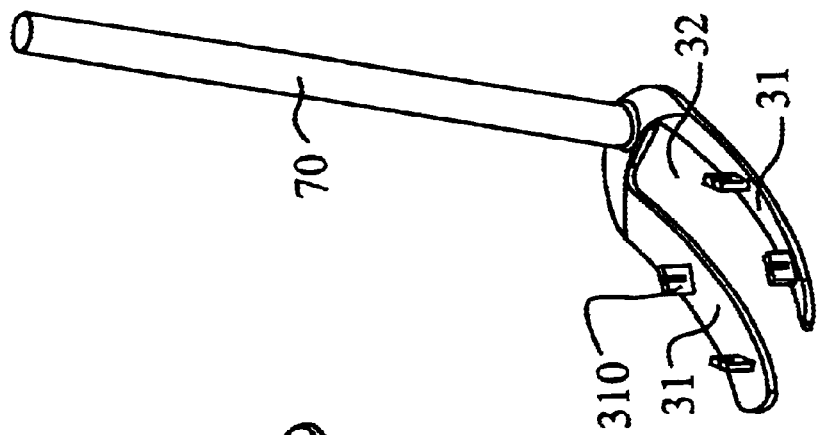
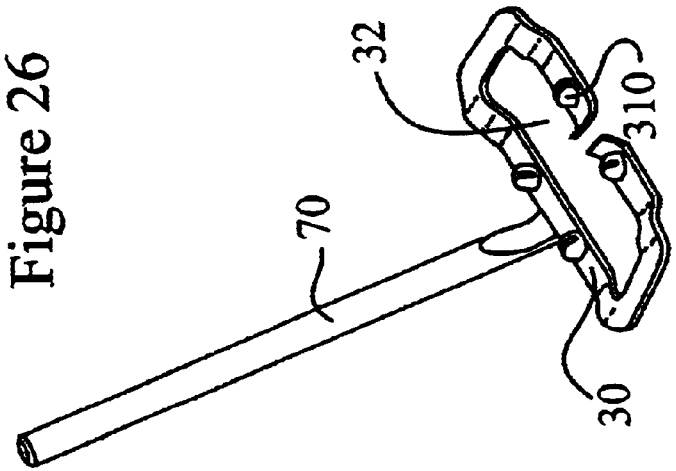

ARTICULATION MEMBER FOR USE IN A SURGICAL APPARATUS

This application is a continuation application of the U.S. patent application Ser. No. 09/482,052, filed on Jan. 13, 2000, now U.S. Pat. No. 6,273,853 which is a continuation of U.S. Application Ser. No. 08/940,766, filed on Sep. 30, 1997 now U.S. Pat. No. 6,102,854.

FIELD OF THE INVENTION

The present invention relates to the field of cardiac surgery instrumentation and more specifically to the surgical method and apparatus optimized for coronary bypass operations.

BACKGROUND OF THE INVENTION

Direct coronary artery revascularization on a beating heart was conducted, both experimentally and clinically, in the 1950's and the 1960's, without stabilization.

Challenges associated with this surgical technique are as follows:

- complete anastomosis is very difficult to achieve due to the motion of the beating heart;
- the technique is limited to vessels of a minimum diameter—again due to difficulty in the anastomosis technique on a beating heart;
- lifting of the heart for revascularization of posterior arteries results in a precipitous drop in arterial pressure;
- the learning curve for surgeons performing this technique is very high; negotiating the learning curve may represent significant surgical morbidity and mortality.

The development of the cardio-pulmonary machine for extracorporeal circulation (ECC) enables coronary operations on an arrested heart. This allows the surgeon to operate on a perfectly still heart and to manipulate the heart to expose the target artery.

At the present time, the standard coronary artery bypass graft (CABG) procedure typically requires a full median sternotomy and extracorporeal circulation through a cardio-pulmonary machine.

Even with the constant technological improvements achieved during the last twenty-five years, the advantages offered with ECC have been offset by morbidity and mortality related to the ECC itself. The inflammatory response, as well as systemic. microembolisms generated by ECC, induce to some extent a dysfunctional state of the brain, lungs and kidneys, which tends to increase with the aging of the patient. Furthermore, evidence suggests that when ECC can be avoided, the left ventricular function is better preserved, thereby reducing risk of post-operative complications.

As a result, alternate CABG procedures that do not rely on the use of ECC offer distinct advantages.

Recently, minimally invasive surgery, involving a partial sternotomy or mini-thorocotomy, has generated much interest since it removes precisely the need for ECC. This surgery does, however, have its limitations. It is adequate for only one or two coronary bypass grafts. Moreover, it does not provide access to the posterior descending or circumflex arteries, and impairs both the anastomosis and the surgeon's vision due to the limited heart exposure.

These limitations may lead to future, more-invasive surgical interventions through partial or full sternotomy, if "blockages" progress in those arteries which were not accessible via minimally invasive procedures.

Therefore, partial revascularization may lead to re-intervention which not only represents a disadvantage to the patient but a financial burden to the health care system.

SUMMARY OF THE INVENTION

It is therefore an object of the present invention to provide a surgical apparatus allowing to perform coronary surgery, in particular coronary artery revascularization, without the need for extra-corporeal circulation.

It is a further object of the invention to provide a surgical apparatus to perform complete revascularization of coronary arteries without the need for extra-corporeal circulation.

It is a further object of the invention to provide a surgical apparatus for performing coronary surgery, in particular coronary artery revascularization, on a beating heart.

It is a further object of the invention to provide a surgical apparatus for performing coronary surgery, in particular coronary artery revascularization, enabling grafting on all arteries of the heart and their respective branches, most particularly the right coronary (RC), the posterior descending artery (PDA), the left anterior descending artery (LAD) and diagonals, the branches of the circumflex artery (Cx) namely the obtuse marginal (1 through 4) and the postero-lateral branches.

It is a further object of the invention to provide a surgical apparatus for performing coronary surgery, in particular coronary artery revascularization, provided with positioning means being capable of being mounted in a plurality of locations on a sternum retractor or any other adequate support.

It is a further object of the invention to provide a surgical apparatus for performing coronary surgery, in particular coronary artery revascularization, simplifying the grafting process.

It is a further object of the invention to provide a surgical apparatus for performing coronary surgery, in particular coronary artery revascularization, with reduced costs associated with shorter time of surgery, reduced costs of surgical equipment, reduced surgical staff, significantly reduced risk of medical complications, and shorter hospital recovery stay.

It is a further object of the invention to provide a surgical apparatus for performing coronary surgery, in particular coronary artery revascularization, that is easy to utilize for surgeons and representing an evolution of current proven practice without the need for long retraining period.

It is a further object of the invention to provide a surgical apparatus for performing coronary surgery, in particular coronary artery revascularization, enabling surgeons to operate on all patients, especially those not well suited to minimally invasive techniques or well suited to conventional coronary artery bypass grafting (CABG) with extra corporeal circulation (ECC).

It is a further object of the invention to provide a surgical apparatus for performing coronary surgery, in particular coronary artery revascularization, with a risk reduced procedure for the patient, a cost effective solution to reducing health care expenses, and an ergonomic layout enhancing the efficiency of surgeons.

It is a further object of the invention to provide a surgical apparatus for performing coronary surgery, in particular coronary artery revascularization, that is ergonomic, easy to deploy, easy to sterilize, and time efficient with respect to the multitude of attachments which might be needed during the course of open chest surgery.

It is a further object of the invention to provide a surgical apparatus for performing coronary surgery, in particular coronary artery revascularization, which optimizes accessibility to all different arteries requiring grafting irrespective of variations in personal physiology from one patient to another.

It is a further object of the invention to provide a surgical apparatus for performing coronary surgery, in particular coronary artery revascularization, that can be used with known types retractors, as a retrofit arrangement.

Another object of the invention is to provide positioning means for a surgical apparatus, in particular a heart stabilizer for performing coronary surgery, particularly coronary artery revascularization, without the need for extra-corporeal circulation.

Another object of the invention is to provide contacting means for a surgical apparatus, in particular a heart stabilizer for performing coronary surgery, particularly coronary artery revascularization, without the need for extra-corporeal circulation.

Another object of the invention is to provide a sternum retractor for performing coronary surgery, particularly coronary artery revascularization, without the need for extra-corporeal circulation.

As embodied and broadly described herein, the invention provides a surgical apparatus for coronary surgery on a patient comprising contacting means being capable of providing a mechanical force against at least a portion of the patient's coronary organs according to its positioning with regard to said organs, positioning means to set said contacting means in a given substantially stable spatial position and orientation within a given volume, said contacting means being pivotingly connected to a sternum retractor via said positioning means.

This surgical apparatus enables performing coronary surgery, particularly coronary artery revascularization, without the need for extra-corporeal circulation. That is to say, the operation can be realized on a beating heart There is no need to use a cardio-pulmonary machine, which considerably reduces the costs of the operation. Without extra-corporeal circulation, mortality and morbidity rates are also reduced.

The surgery and graft process can be performed by only one surgeon and one assistant, as opposed to standard coronary artery bypass graft surgery which usually requires two surgeons and a perfusionist for ECC.

As embodied and broadly described herein, the invention also provides positioning means for a heart stabilizer for use in coronary surgery, said heart stabilizer comprising contacting means intended to provide a mechanical force against at least a portion of the patient's coronary organs according to its positioning with regard to said organs, said positioning means being intended to set contacting means in a given substantially stable spatial position and orientation within a given volume and being connectable in at least one location to a sternum retractor, said contacting means being connectable to a movable free portion of said positioning means.

The contacting means can therefore be positioned in an almost unlimited number of positions and orientations to facilitate the intervention on any artery. This also brings high flexibility, as any patient, whatever the morphology may be, can be treated. Moreover, the adaptability of the apparatus facilitates the grafting process. For example, the right coronary artery is most accessible when the positioning means are mounted on the rack bar. The left anterior descending artery and diagonal arteries are most accessible when positioning means are mounted in the ending portion of the spreader arms. Access to the circumflex artery and posterior descending artery is enhanced when positioning means are mounted on the right side of the retractor, patient's view.

Preferably, the positioning means comprise a sliding member providing relative movement between said sternum retractor and said positioning means. This provides great flexibility and facilitates the surgical manipulations.

As embodied and broadly described herein, the invention also provides positioning means for a heart stabilizer for use in coronary surgery, said heart stabilizer comprising contacting means intended to provide a mechanical force against at least a portion of the patient's coronary organ according to its positioning with regard to said organs, said positioning means being intended to set contacting means in a given substantially stable spatial position and orientation within a given volume and being connectable in at least one location to a sternum retractor, wherein said positioning means comprise an articulation member for providing displacement of a member connected thereof with at least one degree of freedom, a positioning rod connectable to said articulation member, said contacting means being connectable to said positioning rod.

More specifically, under this preferred embodiment, the positioning means comprise a second articulation member for providing displacement of a member connected thereof, with at least one degree of freedom, said positioning rod being connectable to said second articulation member. The articulation member can advantageously be made of a resilient material.

In a specific example, the articulation member comprises at least one partly spherical member pivotingly maintaining a positioning rod member between two hollow cylindrical bodies. In another specific example, the articulation member comprises at least one partly spherical member pivotingly maintaining positioning rod member between two clamping members.

In another specific example, the "quick-assembly" parts allow the positioning means to be placed in at (east six different orientations with respect to the sternum retractor, and consequently the patients heart: four orientations along the perimeter of the retracted chest cavity, and two cross-corner diagonal orientations. This maximizes the options for optimum accessibility to the target artery. It also provides the surgeon with flexibility during delicate surgical tasks like suturing, as he has access to strategic sections of the chest cavity that are free from all devices.

As embodied and broadly described herein, the invention also provides positioning means for a heart stabilizer for use in coronary surgery, said heart stabilizer comprising contacting means intended to provide a mechanical force against at least a portion of the patient's coronary organs according to its positioning with regard to said organs, said positioning means being intended to set contacting means in a given substantially stable spatial position and orientation within a given volume and being connectable in at least one location to a sternum retractor, wherein said positioning means further comprise an articulation member for providing displacement of a member connected thereof with at least one degree of freedom, a positioning rod connectable to said articulation member, a second articulation member for providing displacement of a second member connected thereof with at least one degree of freedom, a second positioning rod connectable to said second articulation member, said contacting means being connectable to said second positioning rod.

As embodied and broadly described herein, the invention also provides contacting means being capable of providing a mechanical force against at least a portion of the patient's coronary organs according to its positioning with regard to said organs within a given volume and comprising two substantially elongated contacting arms defining therebetween an arterial window.

As embodied and broadly described herein, the invention also provides a sternum retractor for use in coronary artery surgery, comprising: a rack bar extending transversally between the ending portions of a fixed spreader arm and a movable spreader arm, these arms both extending longitudinally in a direction substantially normal with regard to the rack bar, said movable arm being capable of being displaced along the rack bar and said spreader arms being provided with blades, contacting means intended to provide a mechanical force against at least a portion of the patient's coronary organs according to its positioning with regard to said organs, positioning means intended to set contacting means in a given substantially stable spatial position and orientation within a given volume and being connectable in at least one location to a sternum retractor, said contacting means being connectable to a movable free portion of said positioning means.

All interfaces are intended and designed to keep the open chest cavity as ergonomic and accessible as possible, free from all peripheral tubing and connectors. All interfaces, design features and components are easy to sterilize.

The surgical equipment described herein can be used to perform multiple revascularizations on any of the coronary arteries or branches without repositioning the sternum retractor after initial deployment. The interfaces between the positioning means and the retractor are preferably designed to permit retractor spreader arm readjustment without disconnecting the positioning means setup. It can be used to perform multiple revascularizations by surgeons experienced in standard on-pump CABG with minimal training. It also can be used to perform revascularizations for both initial surgeries and reoperative cases.

The surgical equipment described herein provides the surgeon with visibility equal to that of standard CABG. Furthermore, in cases where unforeseen complications develop during surgery, the method described herein is not disadvantaged with the delays and complications associated with conversion from a minimally invasive CABG technique to full open chest surgery in cases. It is also not required for the patient to be placed on single lung ventilation, as is the case in some minimally invasive techniques.

The surgical apparatus described herein reduces the costs associated with standard CABG in particular in the following specific areas:
- a cardio-pulmonary machine is not required;
- a perfusionist to operate the cardio-pulmonary machine is not required;
- less highly trained surgical staff is required to perform the surgery (one surgeon and assistant, compared to two surgeons);
- reduced hospital stay is required because ECC is not used;
- reduction in frequency of complications and associated costs;
- reduction in operating time due to ergonomic design features of apparatus.

BRIEF DESCRIPTION OF THE DRAWINGS

The invention will further be described, by way of example only, with reference to the accompanying drawings wherein:

FIG. 4B is a cut away view of the articulation member illustrated in FIG. 4A;

FIG. 4C is a side elevational view of the knob of articulation member illustrated in FIG. 4B;

FIGS. 15A to 15F illustrate several examples of support members for retrofit systems according to the invention, as illustrated in FIG. 14;

FIGS. 26 to 29 illustrate perspective views of contacting means according to the invention;

DESCRIPTION OF THE PREFERRED EMBODIMENTS

Figure 1A:
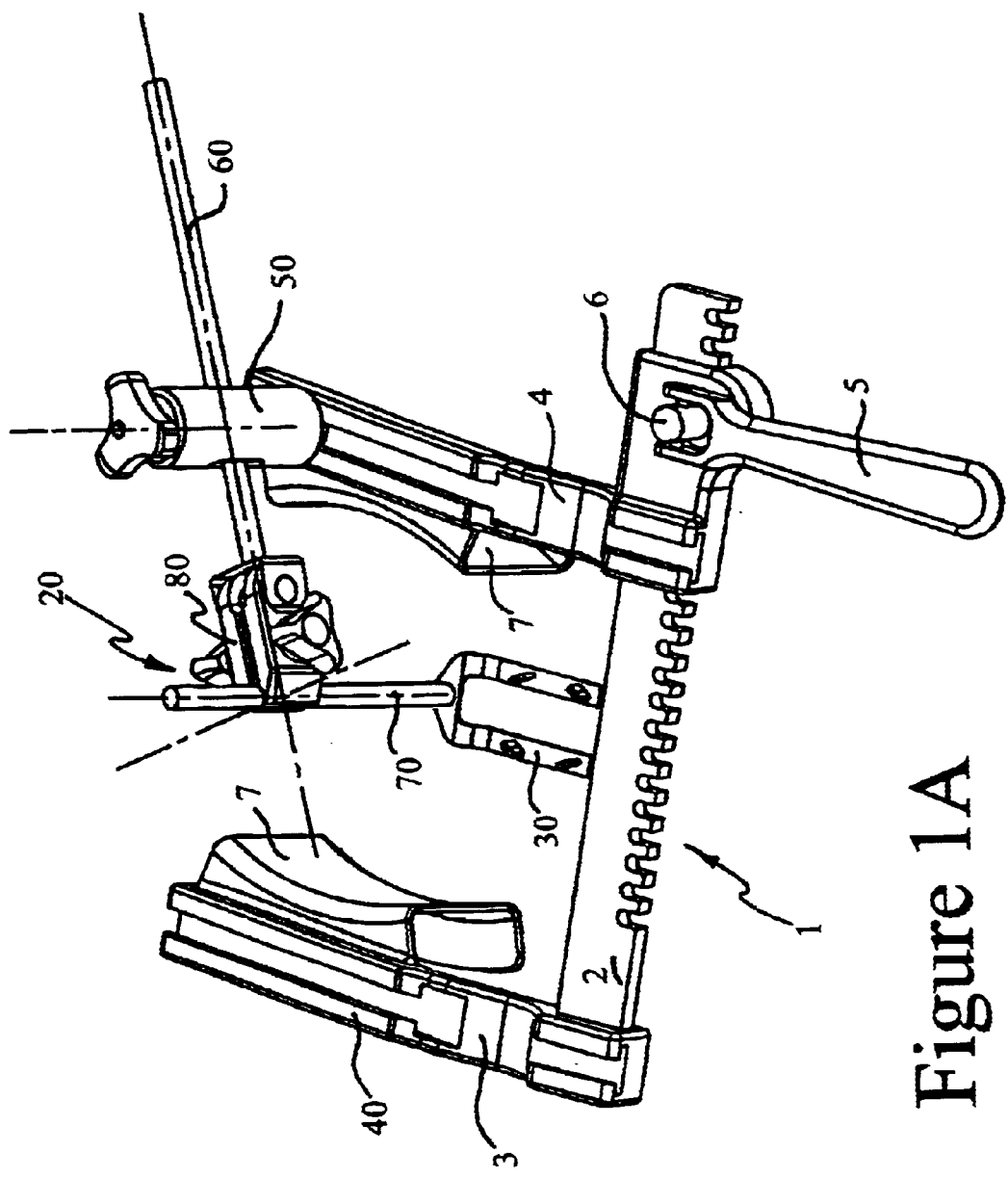
FIG. 1A is a perspective view illustrating a first embodiment of the surgical apparatus according to the invention.

The surgical apparatus according to the invention is provided to be used with a sternum retractor. Single purpose sternum retractors, which only serve to retract the patient's sternum and ribcage, are well known in the art. They are mainly used for retracting the mediastinum in order to perform coronary artery revasculatizations, heart valve replacement, and other cardiac interventions.

Such a sternum retractor 1 comprises a rack bar 2 extending transversally, a fixed spreader arm 3, and a moveable spreader arm 4. Both arms extend longitudinally in a direction substantially normal with regard to the rack bar. The movable arm 4 can be displaced along the rack bar, using a crank 5 activated by a pinion mechanism (not shown) through shaft 6. Two blades 7 are provided underneath the spreader arms.

This invention introduces an improved retractor specifically designed to provide attachment interfaces for a variety of positioning means and any other equipment used during the course of open chest cardiac surgery.

In broad terms, the surgical procedure related to this invention consists of:

1. Full or partial sternotomy;
2. Isolation and removal of either internal saphenous vein(s) or of internal thoracic artery(ies);
3. Strategic positioning and manipulation of beating heart with regard to the artery to be bypassed;
4. Locally immobilizing and stabilizing the portion of the beating heart around the grafting site;
5. "Pinching" the target artery upstream and downstream of occluded site to restrict blood flow during grafting;
6. Grafting of bypass veins and/or arteries;
7. Verifying blood flow through newly grafted bypass artery;
8. Draining of chest cavity;
9. Closing of chest cavity.

In the course of an operation, a surgeon needs to perform certain tasks within the volume defined by the rack bar 2, the arms 3 and 4 and the chest cavity, such as reaching the target arteria, suturing, etc. The volume in which the surgeon needs to perform these different tasks, will be called herein the working volume W. This volume also comprises a buffer zone extending beyond the perimeter of open chest cavity (see FIG. 1B). The present invention provides positioning means 20 allowing the surgeon or an assistant to place and secure a specific surgical instrument, namely the contacting means 30, within this working volume, to perform revascularizations on a beating heart more easily, quickly and effectively. The above mentioned type of retractor is preferably used to set the positioning means. However, other retractor types, for example chest retractor or thoracic retractor, or other supports, for example a bed or a crane, can also be used.

FIG. 1A illustrates a first embodiment in which the positioning means comprise a unique articulation member.

Figure 1B:
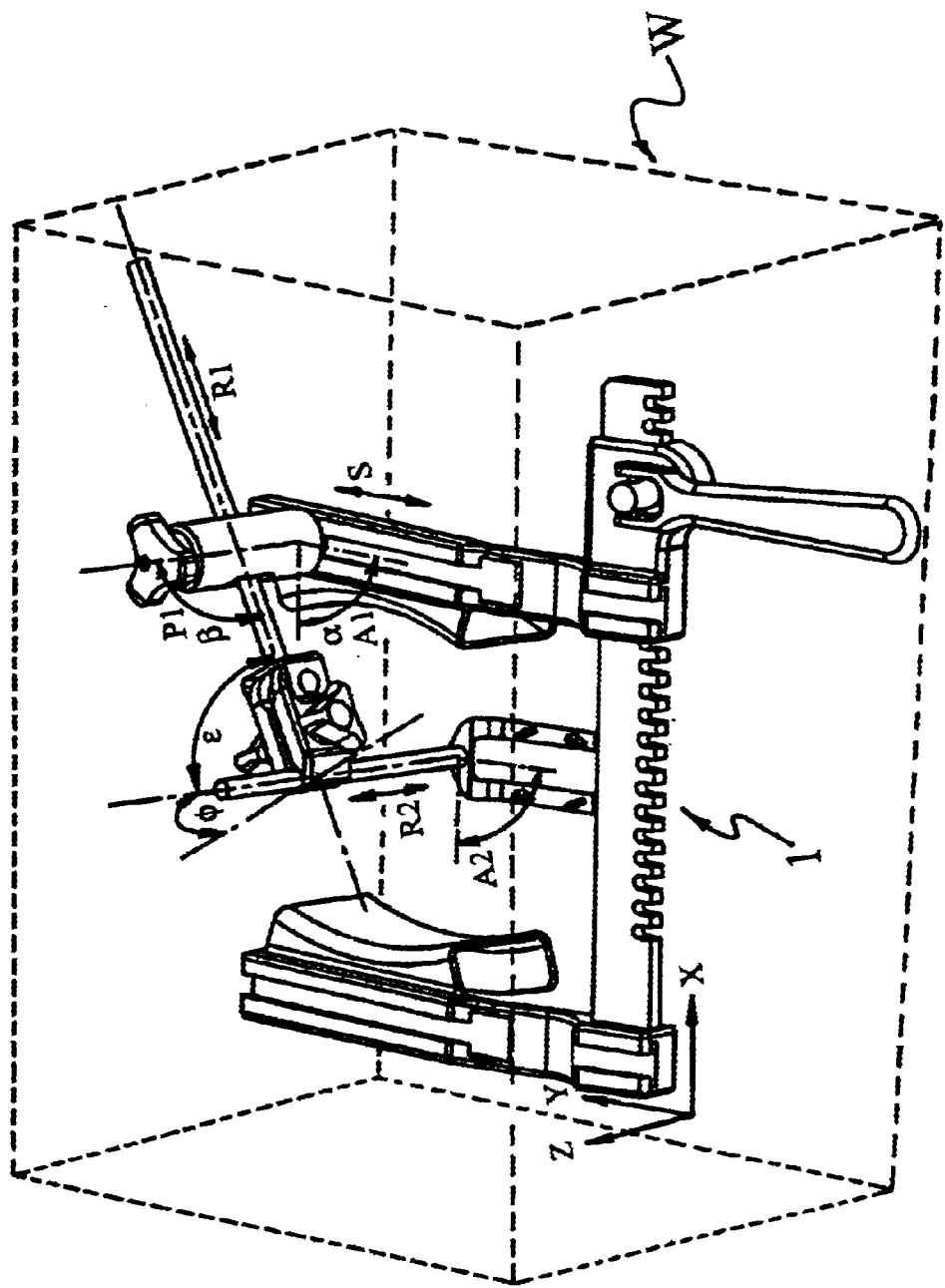
FIG. 1B is a perspective view illustrating working volume W and motion degrees of freedom of the surgical apparatus according to the invention.

FIG. 1B schematically depicts the flexibility and versatility of the surgical apparatus through the motion degrees of freedom listed below:

S displacement of articulation member 50 along rails 40 of retractor;

R1 axial displacement along centerline of first positioning rod 60 through articulation member 50;

R2 displacement along centerline of second positioning rod 70 through articulation member 80;

α rotation about centerline of articulation member assembly 50;

A1 angular displacement through rotation α;

β angle between centerline of first positioning rod 60 and centerline of articulation member assembly 50;

P1 displacement along z axis achieved through rotation β;

ε angle between first positioning rod 60 and second positioning rod 70 in the plane formed by their two axes;

φ angular rotation of second positioning rod 70 in the plane normal to the centerline of first positioning rod 60;

A2 angular displacement of contacting means 30 about the centerline of second positioning rod 70.

The fixed spreader arm and movable spreader arm are preferably provided with rails 40, disposed axially along said arms, for example on top of blades 7. Any known type of rail can be used. FIGS. 22A to 22F illustrate various examples of rail profiles. Other types can also be used like, for example, a rod type rail.

A first articulation member 50 is slidingly and pivotingly engaged in said rails. This first articulation member is easily removable from the rails and can therefore be placed on any of the rails. It can also be set in any axial position on said rails or, alternatively on the rack bar slot as shown on FIG. 17. This first articulation member also serves as a support for a first positioning rod 60. The rod 60 and the articulation member 50 are arranged to allow the free end portion of the rod to be placed in any position within said working volume W. This rod 60 can be easily displaced first with the sliding motion S of the articulation member 50 along any of said rails 40, corresponding to a displacement along the Y axis. Secondly, with an angular motion A1 of the articulation member 50 about its own centerline, the rod 60 can be placed along a given angle α. Thirdly, the rod 60 can be shifted axially (R1) through the member 50 in order to get closer or farther from said member. Finally, the member 50 can also provide a first height positioning P1, allowing the rod 60 to pivot vertically, to reach a given β angle.

The ending portion of this first positioning rod within the working volume is provided with a second articulation member 80. This second articulation member mainly serves as a holding member for a second positioning rod 70. One ending portion of this second positioning rod is provided with a contacting means 30. This second articulation member allows advantageously four types of displacements; first, an axial sliding motion R2 to allow the positioning of the contacting means 30 along the centerline axis of rod 70, within the working volume W; second, an angular displacement A2 of a contacting means 30 about the centerline of positioning rod 70; third, an angular orientation of the second positioning rod 70 with respect to first positioning rod 60 through angle ε; fourth, an angular rotation φ of the second positioning rod 70 in a plane normal to the centerline of the first positioning rod 60. According to a preferred variant, member 50 provides a coarse adjustment whereas member 80 provides a fine adjustment.

In this way, the contacting means can be placed very accurately in practically any position and orientation within said volume W. The position is preferably obtained with displacement S, R1, A1, P1, and R2. The orientation of the contacting means is mainly achieved with the displacement A1, A2, P1, φ and ε. Of course, many variants of the invention can be provided, only by adding or removing a given articulation or displacement possibility. For example, the first transmission member 50 could be provided so that rod 60 rotates along its own axis, or contacting means 30 could be provided with a pivot at its junction with rod 70, etc. Furthermore, the positioning means extends advantageously beyond the perimeter of the open chest cavity.

Different types of articulations may be used for the first articulation member 50 and second articulation member 80. For example, known types of articulations like resilient articulations or spherical bearing articulations, etc, may be used without departing from the spirit of the invention. The articulations used with the embodiment illustrated in FIG. 1A are shown in details in FIGS. 3 and 4A.

Figure 3:
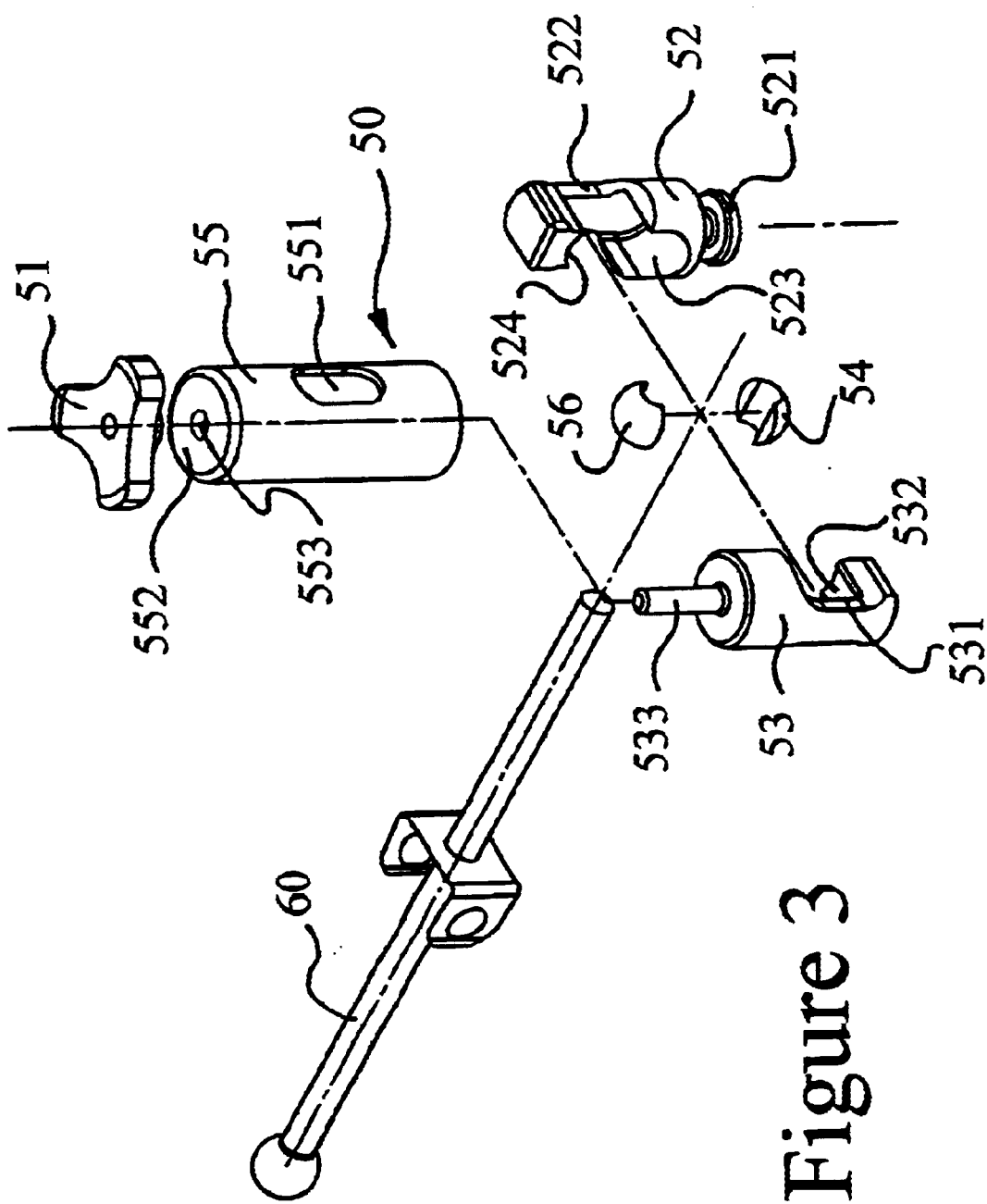
FIG. 3 is an exploded view of the first articulation member used in FIG. 1A.

FIG. 3 illustrates an exploded view of an example of a first articulation member, such as the one used in the embodiment of FIG. 1, with reference 50. A hollow cylindrical body 55 is provided along its longitudinal wall with two opposite oval windows 551. A top cover 552 on the upper end is provided with a central aperture 553. A bottom hollow cylindrical member 52 is provided with two opposite lateral openings 522. The front portion is open to cooperate with other components. The inner top and bottom portions are shaped with opposite concave profiles 524 and 523. Two opposite semi-sphere like adaptors 56 and 54 are provided with a cylindrical hollow. A top hollow cylindrical member 53 is provided with lateral openings corresponding susbtantially to those of the hollow cylindrical member 52 so that it can cooperate with the bottom member 52. On top of member 53 a screw member 533 is provided. The inner bottom portion is shaped with a concave profile corresponding to the lower semi-sphere like adaptor. The positioning rod is engaged through the hollow portion of the two semi-sphere like adaptors to create an assembly.

This assembly is placed in the cavity formed by the cooperating members 52 and 53. The upper and lower adaptors 56 and 54 cooperate respectively with the concave inner portion 524 and the concave inner portion 532. This allows easy pivoting of the rod, not only vertically, but also laterally. All these components are maintained together in the cylindrical body 55. The rod extends through windows 551. Screw member 533 extends through aperture 553 and cooperates with set screw 51. A flange 521 provided at the bottom of member 52 allows easy engagement of the assembly within rails 40 or any attachment means, that do not necessarily provide sliding possibilities.

When the set screw is loose, cooperating components allow pivoting movement of the rod and eventually a rotational movement of the latter along its own axis. When the screw is tightened, a compression stress is generated with the inner portion 532 of member 53 pressing against adaptors 54 and 56 and inner portion 524 of member 52. A tight fit is therefore created into the cylinder body 55. This mechanical stress avoids any relative movement of the components. Moreover, the body 55 is pressed against the spreader arm or rail or the like on which it is engaged, creating a locking effect. The articulation is then slidingly and pivotingly locked.

Figure 4A:
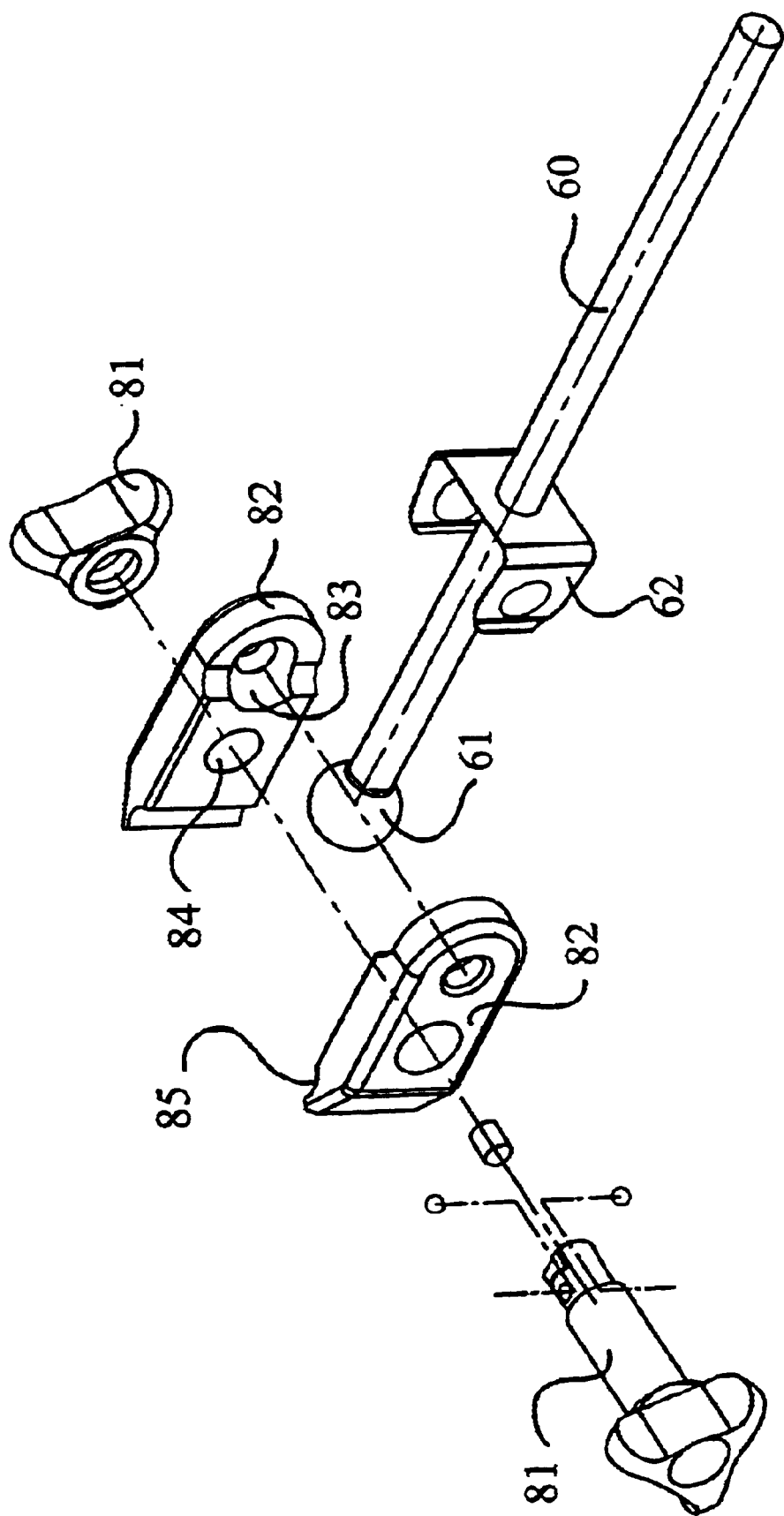
FIG. 4A is an exploded view of FIG. 1.

FIGS. 4A to 4C illustrate views of an example of an articulation member such as the one used in the embodiment of FIG. 1, with reference 80. The figures shows two elongated and opposite clamping members 82, each one provided with an inner seat portion 83 to cooperate with a ball end 61 on rod 60, and an aperture 84 for engagement of set screw member 81. An inner annular groove 85 is also provided for engagement of the second positioning rod 70. The groove 85 is arranged in a direction substantially perpendicular with regard to the longitudinal axis of the clamping members 82. A preload spring 62 ensures that the members 82 and 61 are properly maintained as an assembly. Moreover, the two members 82 are tightened together with screw member 81.

They provide a housing for ball end 61 and a portion of rod 70. Depending on the tightening of screw member 81, the articulation maintains the rods 60 and 70 in a locked or mobile arrangement. The angular movements ε and φ of positioning rod 70 are achieved through relative movement of members 82 with respect to 61. Screw member 81 is preferably provided with an arrangement that gives the possibility to adjust the positioning by using either side of screw member 81. This feature is advantageous because the working area W is in general very small and the access to a specific side of the screw member 81 is limited for the surgeon.

FIGS. 4B and 4C illustrate such an arrangement. Left side knob 801 extends longitudinally with threaded rod 802 through the left clamping member 82 and is screwed to the right clamping member which is provided with inner thread 806. The end portion of rod 802 and the corresponding inner portion of knob 801 are shaped with two opposite flat surfaces 803, allowing torque transmission from the knob to the rod. Locking balls 805 provided in a circular groove in the inner portion of right side knob and maintained with a set screw 804 keep the components together. With such an arrangement, the surgeon tightens or untightens the two clamping members 82 by actuating any of the two knobs 801. The rotational movement allows inner threads 806 to create a translational movement of corresponding right clamping member 82, that will therefore get closer or farther from the other facing clamping member, resulting in a tightening and loosing effect.

With these various adjustment possibilities, the contacting means 30 can easily be positioned very accurately with regard to the target arteria of the heart. Moreover, according to a variant, a coarse adjustment is performed with one articulation member (for instance the first articulation member 50) and a fine adjustment is achieved with the other articulation member (for instance the second articulation member 80).

Figure 5A:
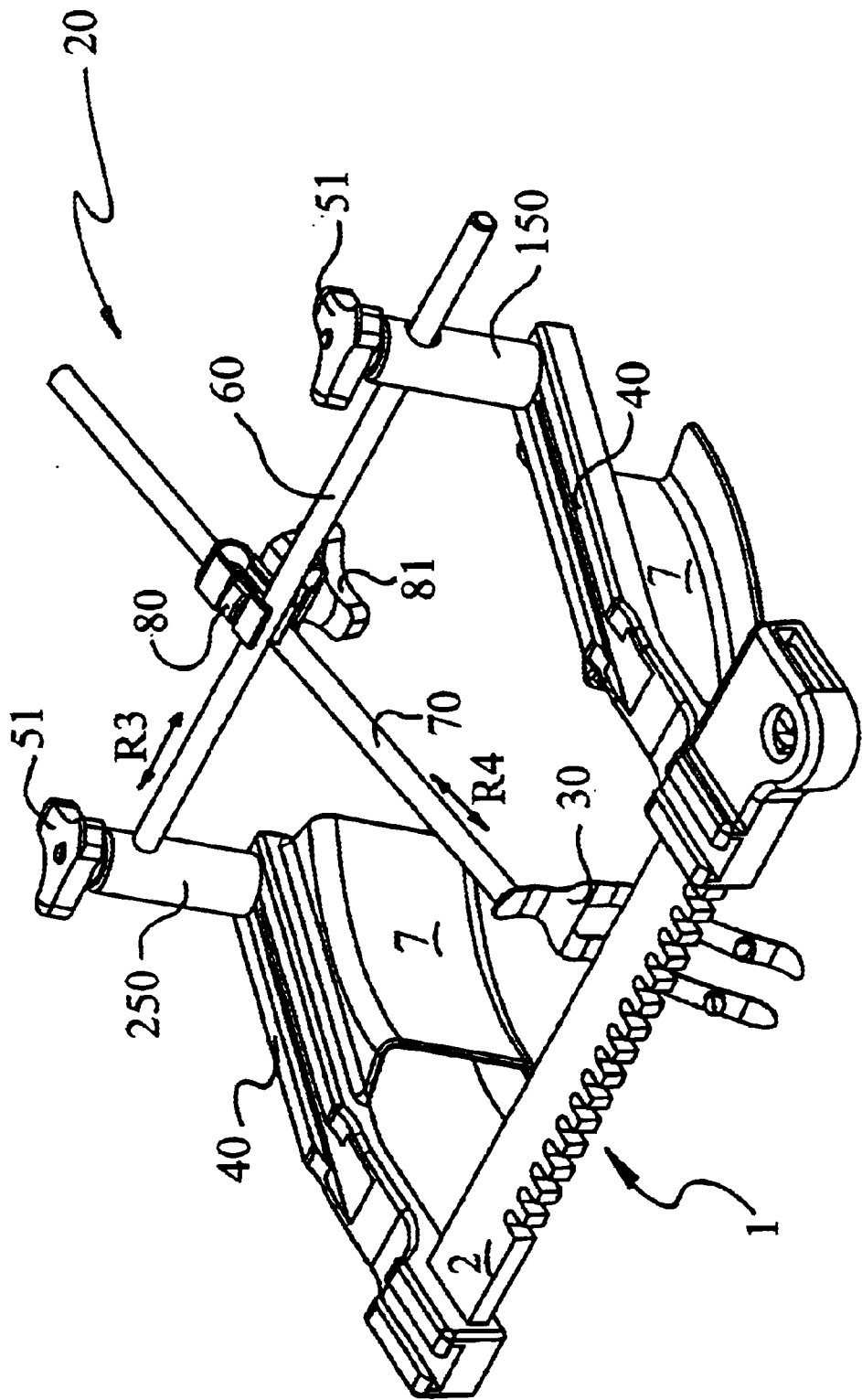
FIG. 5A is a perspective view illustrating a second embodiment of a surgical apparatus according to the invention.

FIG. 5A illustrates a second preferred embodiment according to the invention. The sternum retractor arrangement is similar to the previously described one. However, the positioning means 20 slightly differs from the first embodiment. According to this second embodiment, two articulation members 150 and 250 are provided. These articulations may be in many aspects similar to those described above.

Figure 5B:
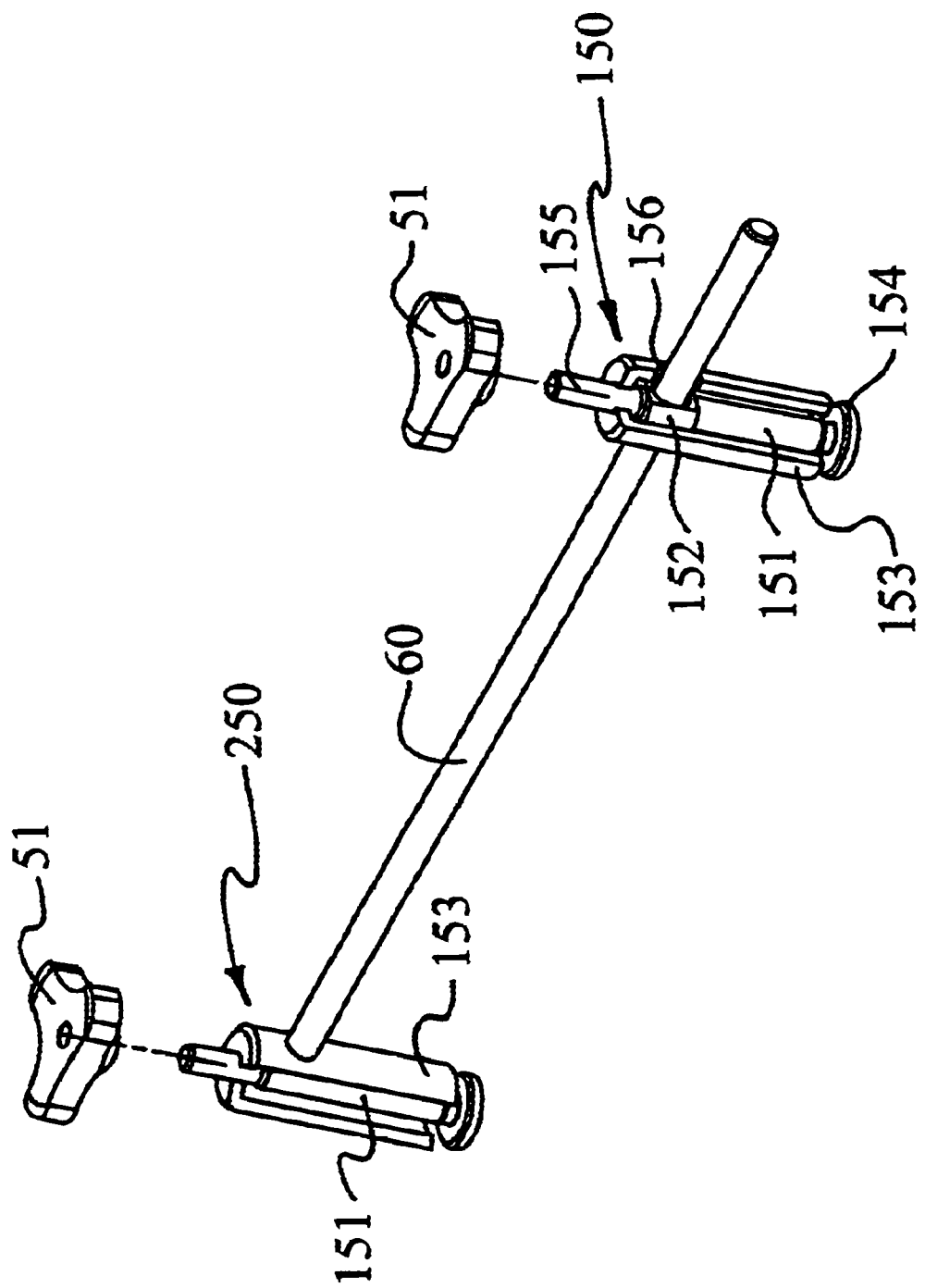
FIG. 5B is a perspective view (partly cut away) of the articulation members used in FIG. 5A.

FIG. 5B is a perspective view, partly cut away, illustrating the articulation members 150 and 250, and the first positioning rod 60. One articulation member is arranged to allow a sliding movement of the positioning rod through it. An inner rod member 151 is provided with a transversal hole 152 seated in a hollow cylindrical body 153, with two open ends 156. A threaded portion 155 extends upwardly beyond the body for engagement with a set screw 51. The bottom portion extends downwardly beyond the body and is provided with a flange 154 for engagement with rails 40.

When set screw 51 is tightened, a tensile strain causes the bottom edge of the cylinder body 153 to press against the edge of windows 156 through which rod 60 extends. The same strain causes the bottom edge of the cylinder body 153 and the upper edge of flange 154 to press against the rails 40 in opposite directions. The assembly is therefore locked. When set screw is loose, no strain acts against the components. The rod can slide through the articulation and the articulation is capable of sliding and/or pivoting along the rails. The opposite articulation member 250 can be similar to the one described above or can be simplified by having rod 60 in a fixed configuration on relative to articulation member 250. This can be achieved with an assembly comprising an inner rod member 151 and a cylinder body 153 similar to those previously described. The rod is then attached to the cylinder body. This allows sliding and/or pivoting movement of the articulation member 250 along the rail 40. One or both articulations can be displaced along the rails or placed on discrete locations on the retractor, if no rails are provided.

The articulations can be set in a symetric disposition, with each articulation having an identical position with respect to the rack bar. They can also be arranged in asymetrical disposition, on the same arm, etc., as shown in FIG. 13. The translational motion of the rod 60 through the articulation 150 remains an advantageous feature of this embodiment. For example, if during surgery, the sternum retractor opening must be modified, the rod 60 can slide through one of the articulations (for instance, the articulation engaged in the movable spreader arm), allowing the second positioning rod 70 and the contacting means 30 to remain in substantially the same position with regard to the heart This allows efficient readjustment of the surgical apparatus without complete disassembly of the positioning means.

Figure 2:
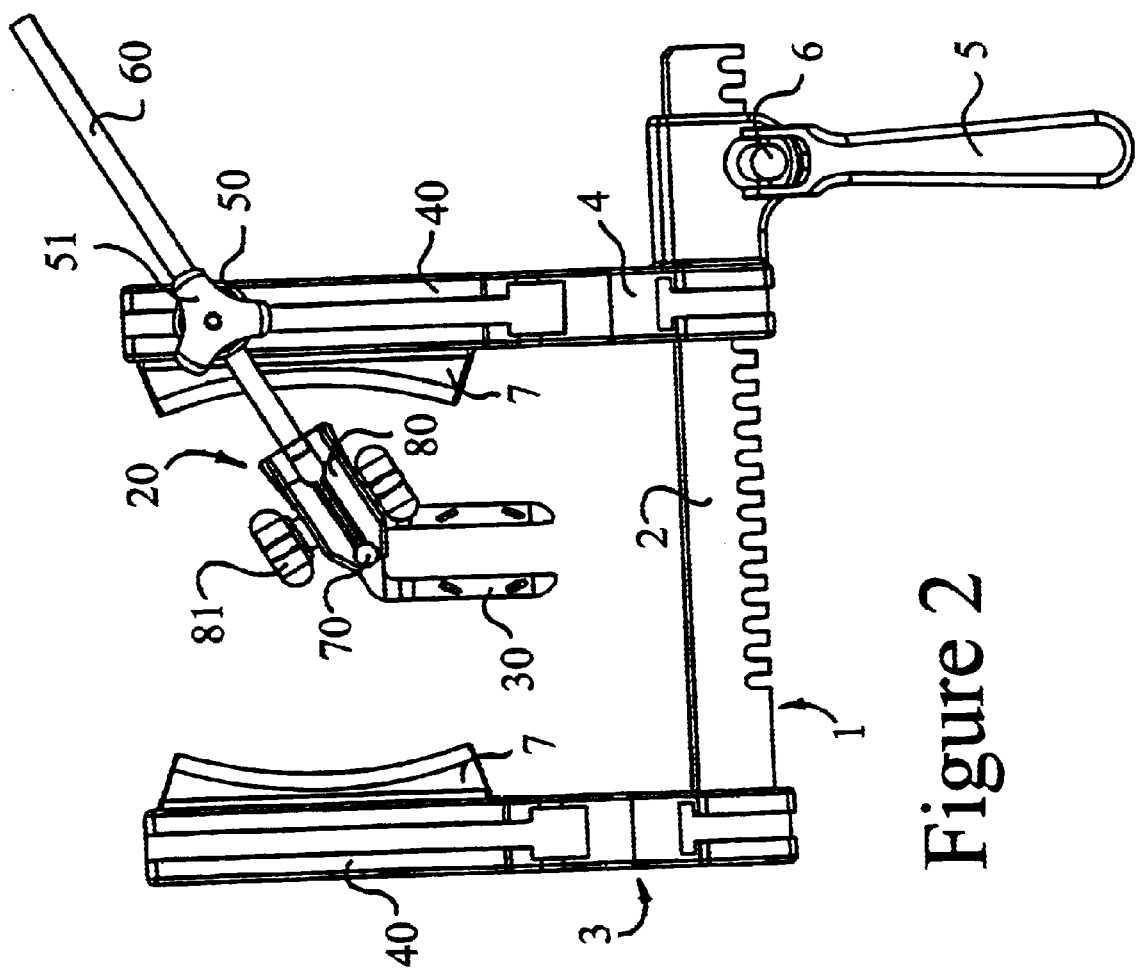
FIG. 2 is a top view of the embodiment illustrated in FIG. 1A.

Of course, with such an embodiment, the second articulation member 80 is slightly different from the one described above (shown in FIG. 2). This second articulation member allows advantageously five types of displacements: first, an axial sliding motion R3 to allow the positioning of the second rod 70 along the centerline axis of rod 60; second, an axial sliding motion R4 to allow the positioning of the second rod 70 through articulation member 80; third, an angular rotation of the contacting means 30 about the rod 70 axis; fourth, in the plane defined by the axes of the rods 60 and 70, angular orientation of said rods; fifth, angular rotation of rod 70 around the axis of rod 60. The set screw 81 allows for easy setting and readjustment of rod 70 with respect to rod 60. The contacting means 30 is provided at the end portion of the rod 70, within the working volume W. The rails 40 can eventually be extended with a separate rail portion placed on the rack bar.

Figure 6:
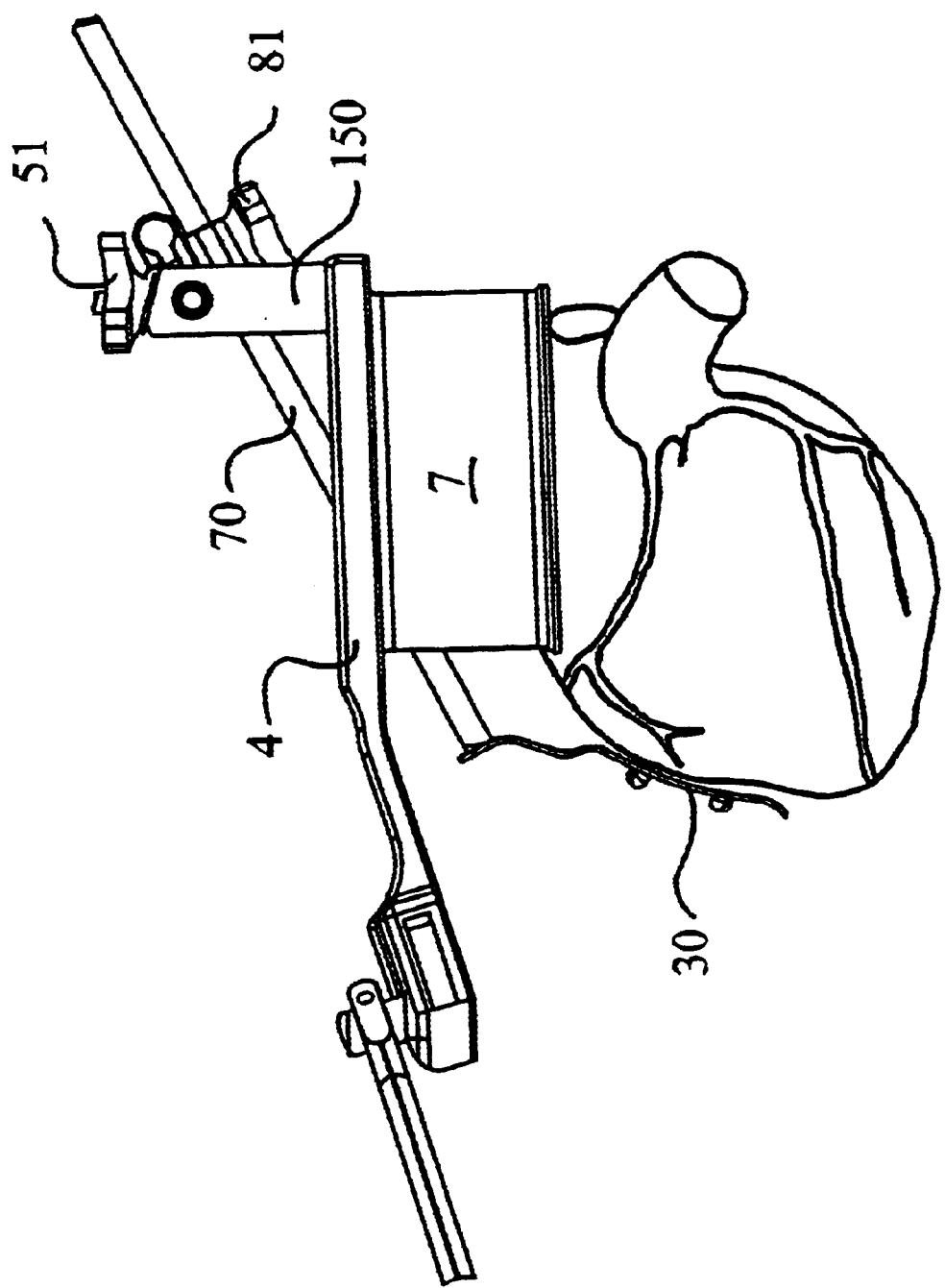
FIG. 6 is a side elevational view of the embodiment illustrated in FIG. 5A.

FIG. 6 illustrates a transversal view of this embodiment. From this drawing, it can be seen that the contacting means 30 has a very specific shape. In this particular embodiment, the slightly curved profile allows the positioning of the contacting means with regard to the heart, so that the heart is placed in the concave side of the contacting means. With such an arrangement, the positioning means is capable of producing a pulling force against the heart. These features will be described thoroughly herein below.

Figure 7:
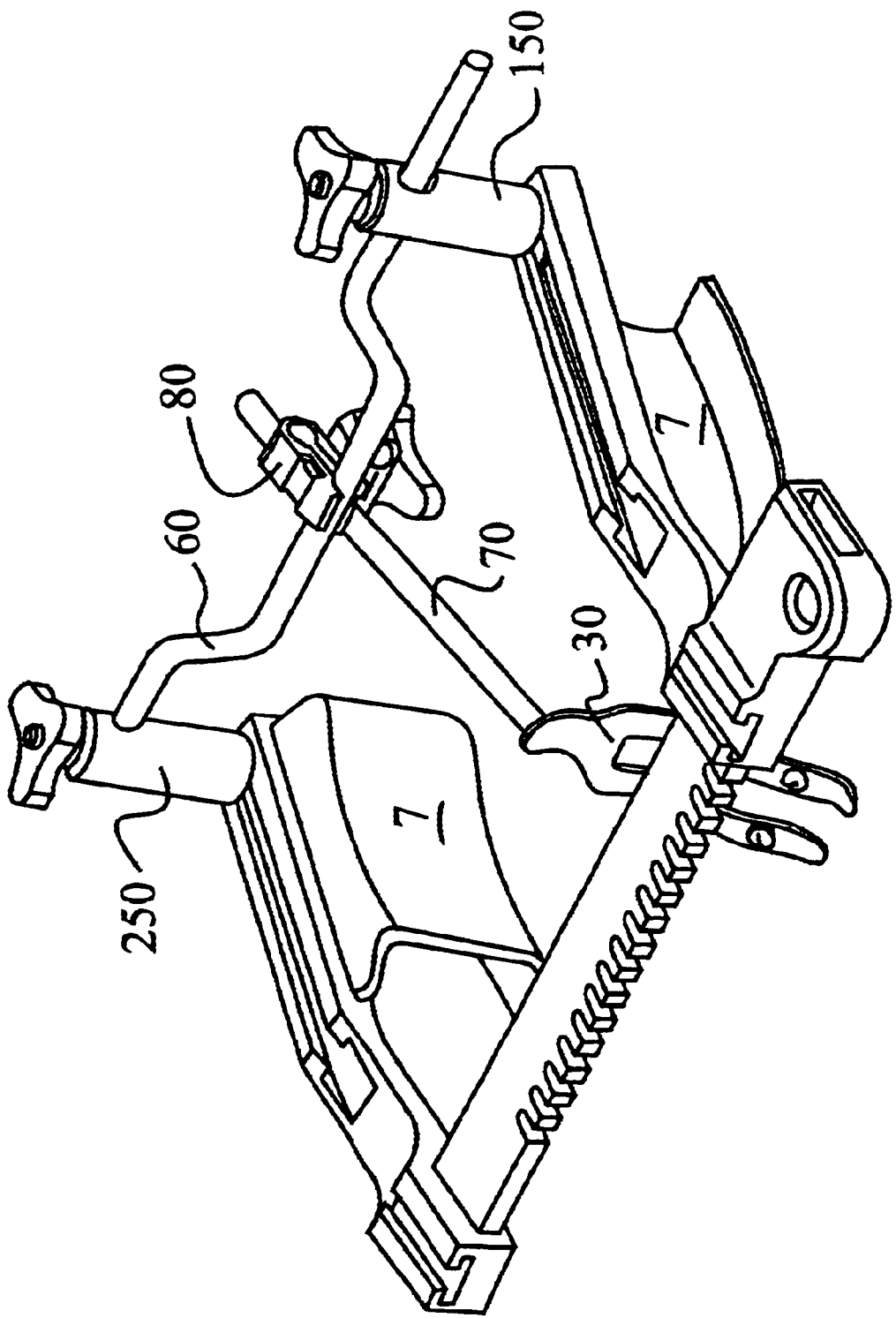
FIG. 7 is a variant of the embodiment in FIG. 5A.

FIG. 7 shows a variant of the previous embodiment According to this variant, the rod 60 is bent to form a U-shape with regard to the two articulation members. Such a shape gives additional adjustment possibilities to position the contacting means with regard to the heart.

Figure 8:
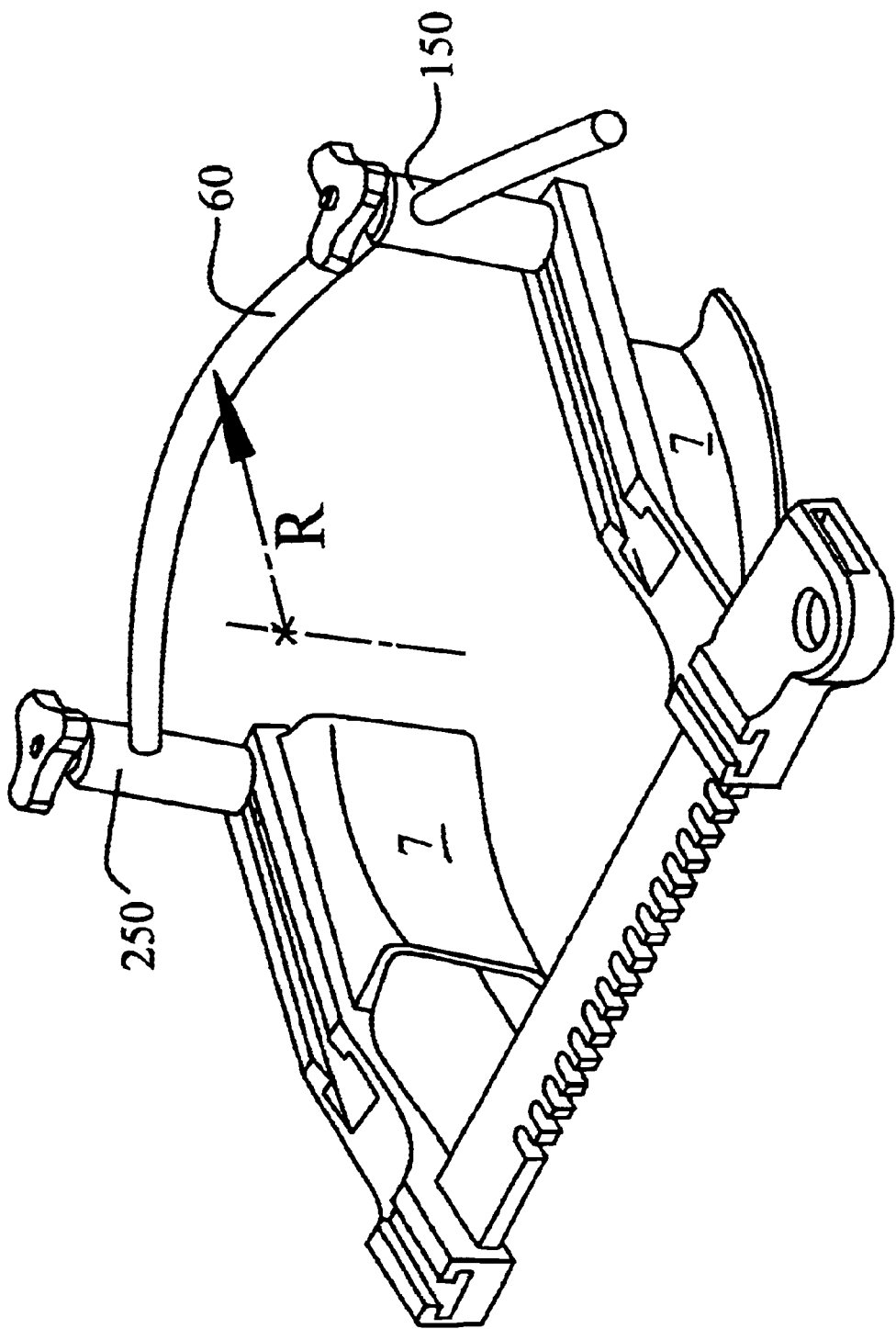
FIG. 8 is another variant of the embodiment of FIG. 5A.

FIG. 8 illustrates a further variant of the embodiment illustrated in FIG. 5A According to this variant, the rod 60 is shaped in the form of a circular arc. The letter "R" on the figure illustrates the radius of the corresponding virtual circle. Once again, this particular shape allows a very accurate positioning of the contacting means with regard to the target artery.

Figure 9:
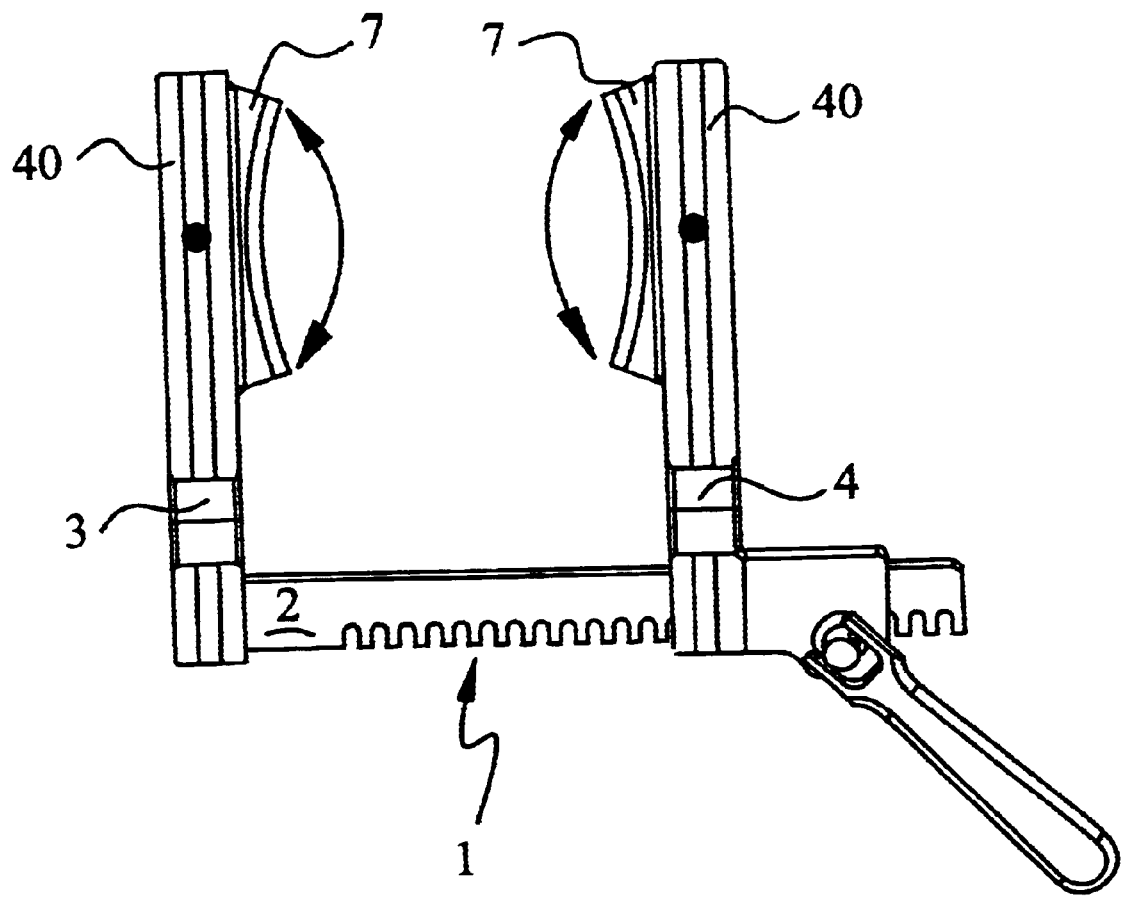
FIG. 9 is a variant of the embodiments of FIG. 1A and FIG. 5A.

FIG. 9 illustrates a top view of a variant whereas one or both blades 7 are rotatably mounted on the retractor arms. The remaining features being similar to those already described are not illustrated. This variant is advantageous while it gives a possibility to adapt the blade arrangement to the sternum of the patient to be treated, without affecting the remaining components of the apparatus. For example, one blade could be installed slightly rotated with regard to the other one.

According to the invention, the surgical apparatus advantageously provides anchoring means disposed in discrete positions along the arms 3 and 4 or possibly at any other location on the device. FIGS. 10A through F illustrate different variants of such anchoring means. These anchoring means serve many purposes, for example to attach "in-process" sutures that are strategically used to position tissue or organs away from primary surgical operation; to attach Silastic™ rubber bands, or silicon loops, utilized during myocardial mobilization, or pericardial traction; to attach sutures or silicon rubber loops, serving to "brace" the positioning means rod in significantly overhung orientations with respect to the retractor; and to secure any peripheral equipment used during operation to keep uncluttered chest cavity during surgery. These anchoring means are intended to allow a quick assembly and disassembly of the wire, suture, Silastic™ rubber bands, etc.

Figures 10A, 10B:
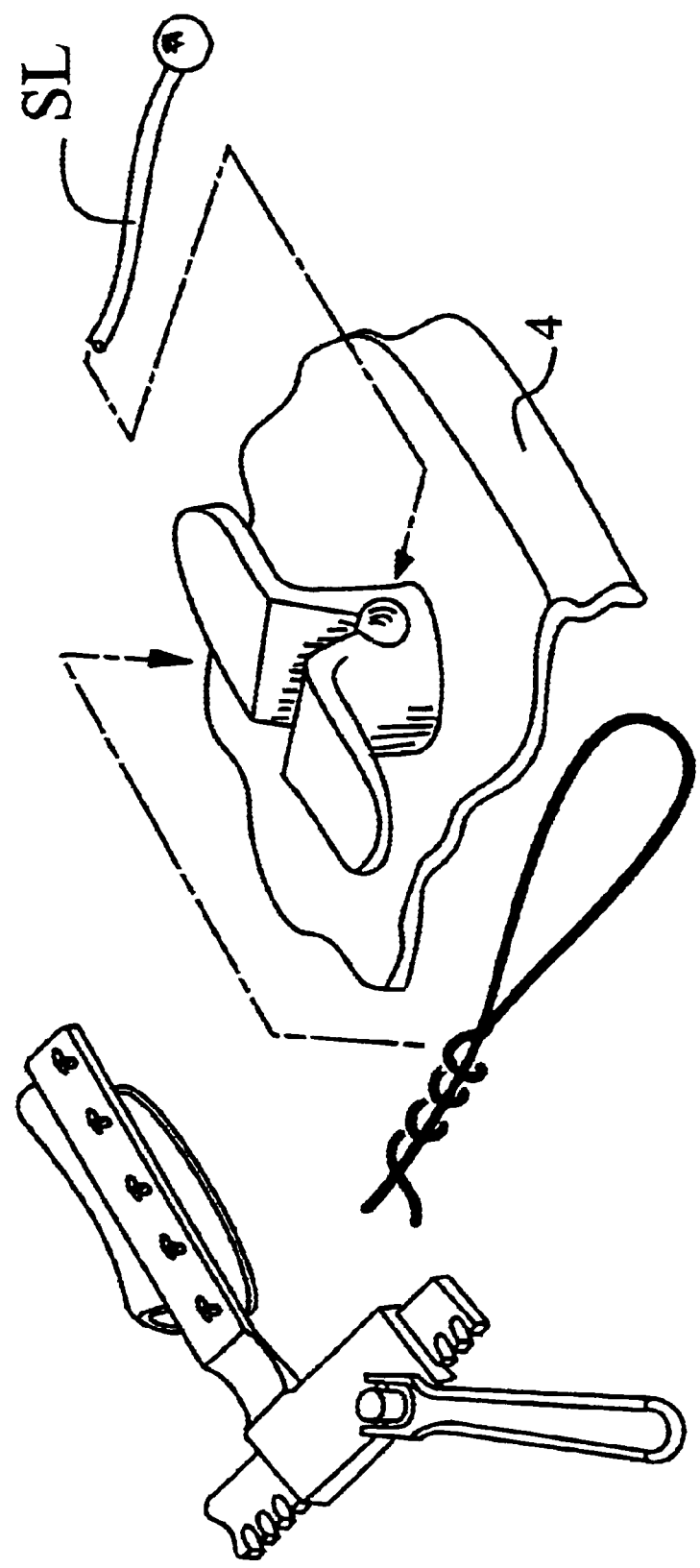
FIGS. 10A to 10F are perspective views according to the invention.

FIG. 10A shows an example of an arrangement with such means preferably disposed along a rail. FIG. 10B illustrates an example of an anchoring means with a "V" shaped aperture in which the wire can be inserted very quickly. At the base of the "V", a slightly enlarged opening provides a seat to lock the wire. Each side of the "V" shape is provided with a blade, retaining the wire that is wounded-up around the body of the means.

Figures 10C, 10D, 10E, 10F:
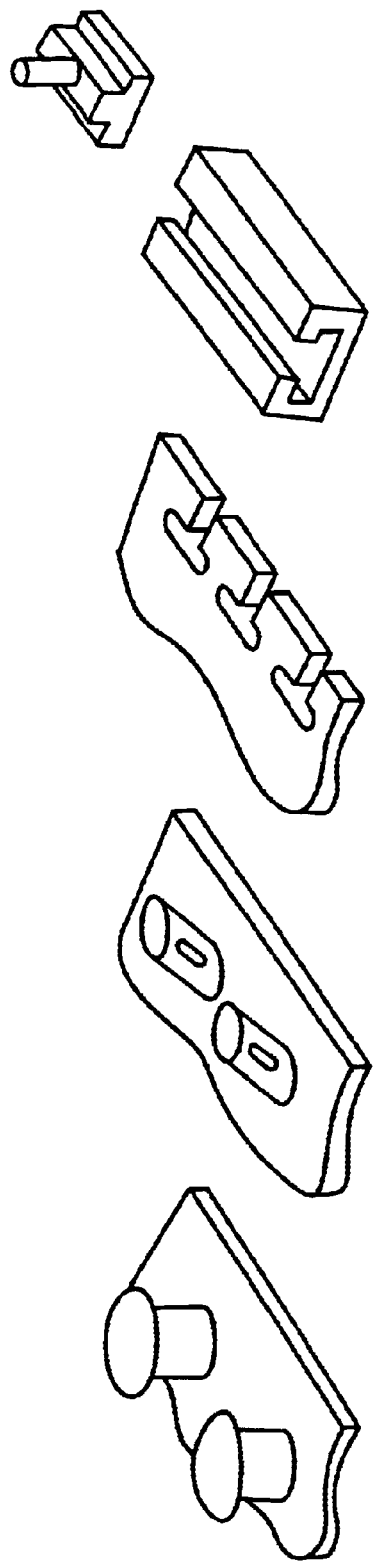

FIG. 10C illustrates a different shape of anchoring means with a nail like head. FIG. 10D illustrates another variant which is shaped like an inclined rod. FIG. 10E illustrates anchoring means consisting of T-shape apertures provided in the spreader arm or in any other location of the surgical apparatus. FIG. 10F illustrates a pin type anchoring means. As illustrated the pin is advantageously slidingly arranged.

Figure 11:
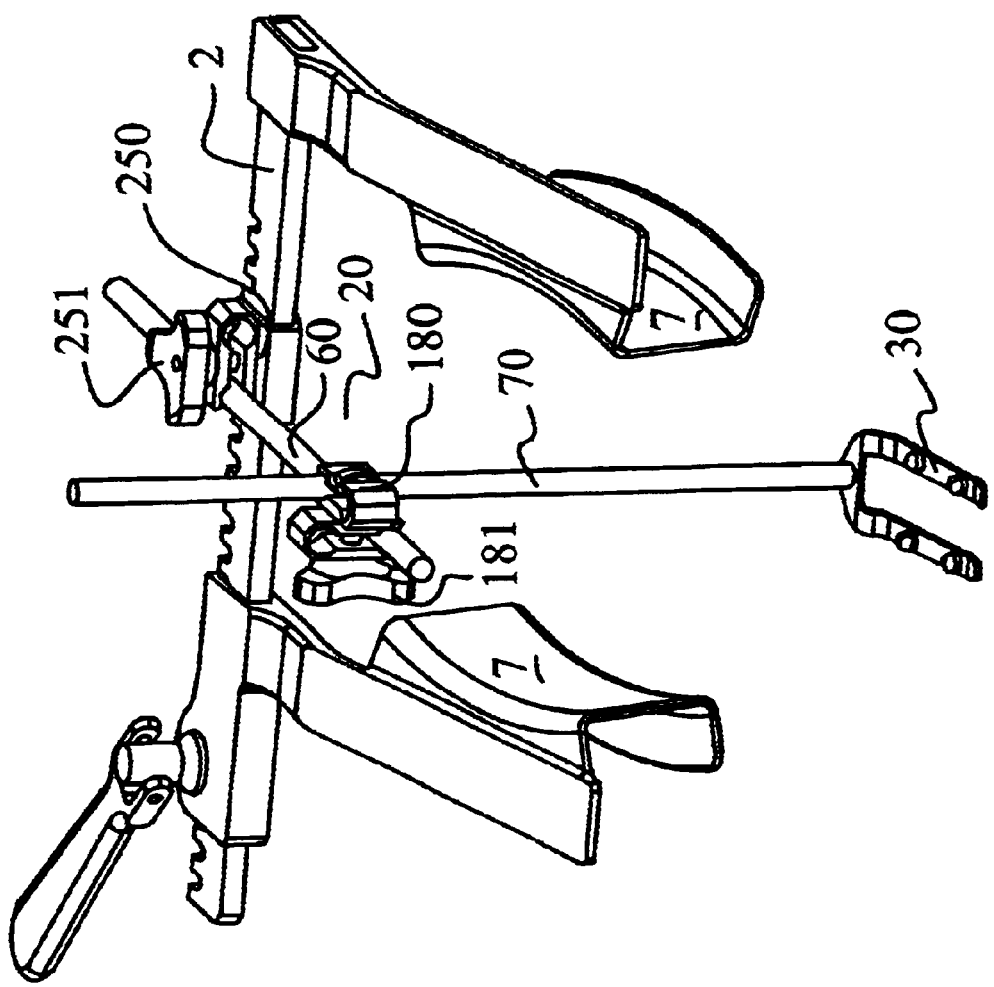
FIG. 11 is another embodiment of the surgical apparatus.
Figure 12:
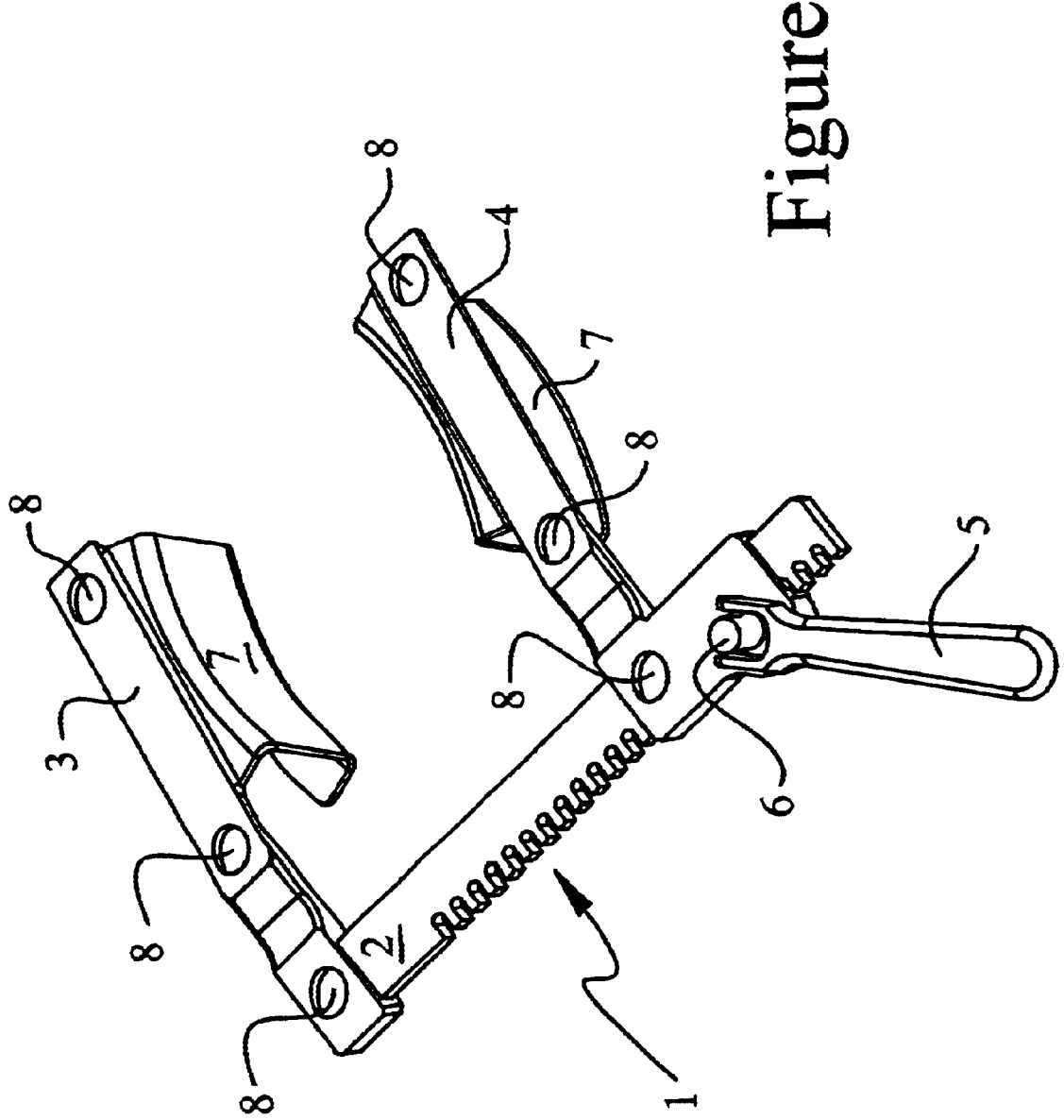
FIG. 12 is a perspective view of a sternum retractor variant.
Figure 13A:
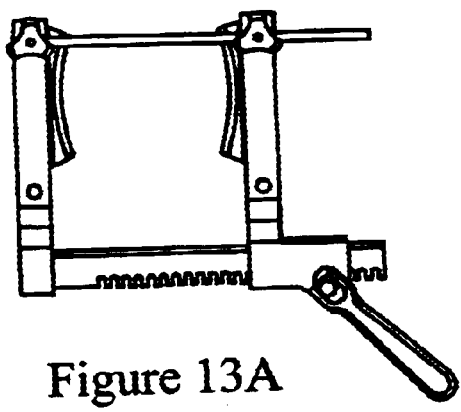
FIGS. 13A to 13F illustrate examples of several setting possibilities of the positioning members on a sternum retractor, as illustrated on FIG. 12.
Figure 13B:
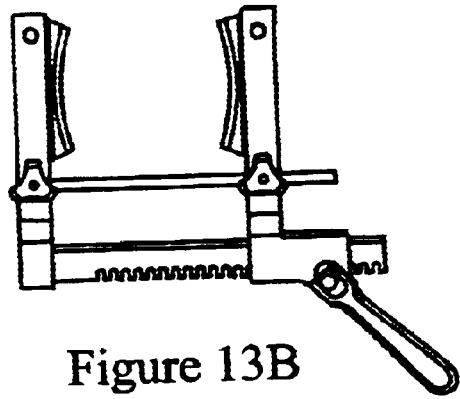
Figure 13C:
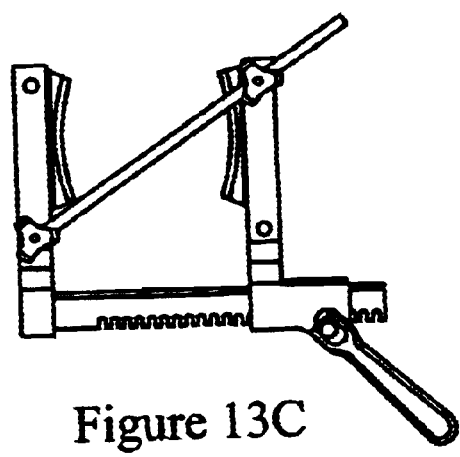
Figure 13D:
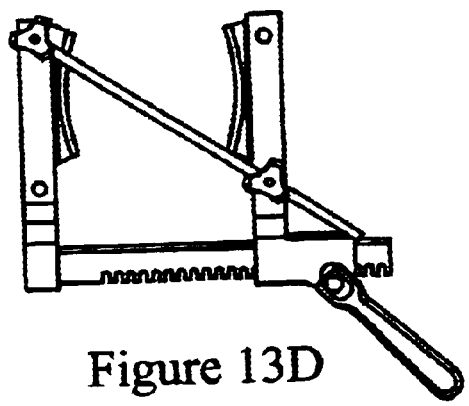
Figure 13E:
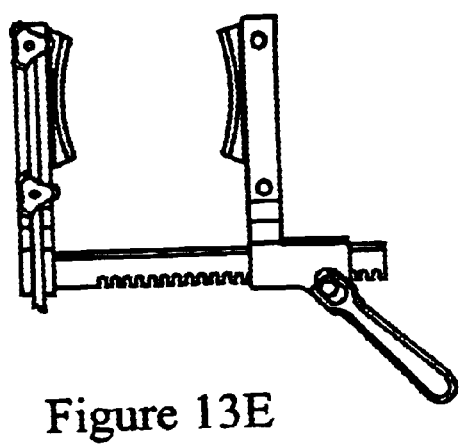
Figure 13F:
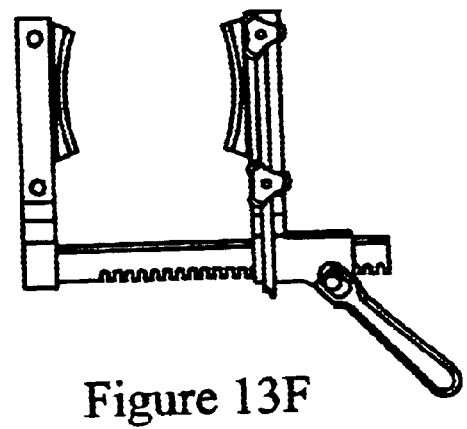

FIG. 11 illustrates a third embodiment of a heart stabilizer according to the invention. This simplified embodiment uses a standard sternum retractor. The positioning means 20 are connected to the sternum retractor through an articulation member 250 attachable to the rack bar of the retractor. According to the embodiment illustrated in FIG. 11, the articulation member consists of a "U" shaped sliding member, laterally inserted into the rack bar 2. A set screw 251 allows to lock or unlock the articulation member on the rack bar. The unlocked position allows the surgeon to slide the assembly on either side of the bar. It also permits him to slide the first positioning rod 60 axially. It also allows him to slidingly and pivotingly set rod 60 with respect to rack bar 2 through articulation member 250. The set screw 251 allows an easy longitudinally positioning of the assembly.

The axial positioning can be set either with the articulation member through set screw 251 or with the second articulation member 180 through a set screw 181, though this second articulation member mainly serves to angularly position a second positioning rod 70. This angular position can be easily modified as the two clamps are pivotally connected together. The contacting member 30 is provided at the ending portion of this rod located within the working volume W.

The characteristics related to the rods and second articulation member are similar to the second embodiment illustrated in FIG. 5A and described above. This very simple attachment means allows the use of a heart stabilizer according to the invention with an existing sternum retractor. Such a "retro-fit" is very advantageous while most hospitals or clinics are already equipped with retractors. This existing equipment can thus be updated. This embodiment can also feature quick connect/disconnect articulations, as described below.

FIGS. 12 to 15 illustrate a further embodiment particularly suited to retrofit applications but not exclusively reserved for them. A known type sternum retractor 1 may be used. According to the invention, the retractor is easily modified to provide attachment means, such as for example attachment holes 8 preferably located by each end portion of the spreader arms and/or arranged in discrete locations along the retractor.

Different types of stabilizer can then be used to complete the arrangement. For example, a stabilizer with positioning means such as described above for the embodiments of FIG. 1A or 5A The attachment means could serve to attach rails, that for example are similar to those of FIG. 1 or 5, or an assembly without rails, the articulation member being attachable to any of the retractor holes 8.

Figure 14:
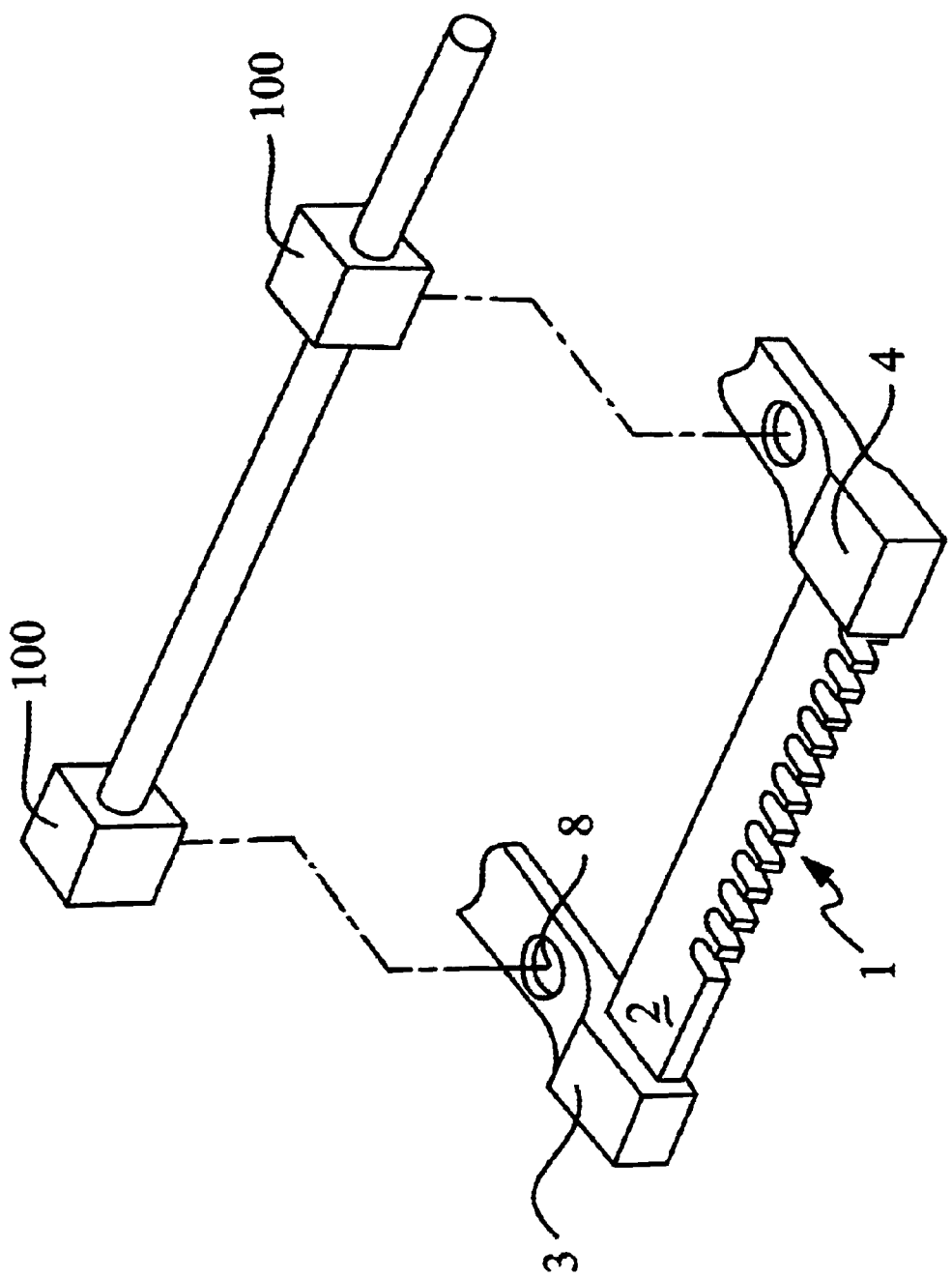
FIG. 14 is a perspective view partly exploded and schematically illustrating an example of a retrofit system according to the invention.
Figure 16:
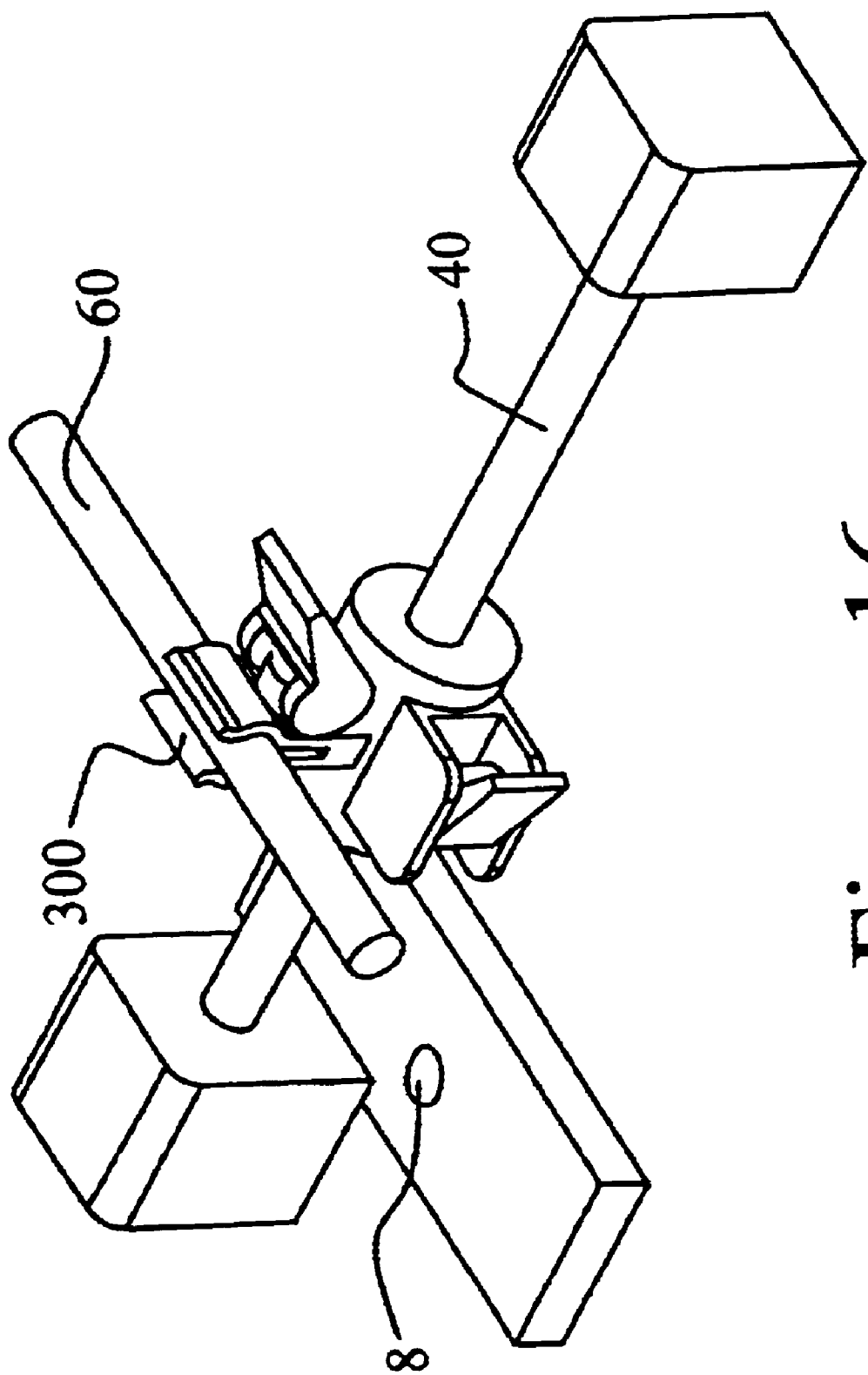
FIG. 16 is a perspective view illustrating a further embodiment of the surgical apparatus according to the invention, using easy to connect/disconnect articulation members.

FIGS. 14, 15, and 16 illustrate examples of attachments to the retractor. FIG. 14 shows an example with two supports onto which the rail is attached. The rail could be of a rod type, as shown in FIG. 14, or sliding type as shown in FIG. 1A, or any other appropriate type. FIG. 15A illustrates an example of a support provided with a rubber boot 101, a rod 102, and a locking system actuated by a cam-lock. The system is illustrated in the locked mode, in which the rubber expansion fills the surrounding cavity creating thus a locking effect.

FIG. 15B illustrates a magnetic type of support which offers the advantage to avoid the holes on the retractor in the previous examples. The holes are replaced by a magnetic insert 111, on which the magnetic support can be placed. The magnetic support 110 preferably comprises a layer arrangement with alternate layers of magnetic 112 and non-magnetic 113 alloy. A portion of the layer assembly is transversally movable with regard to the remaining portion. Buttons 114 allow the surgeon or user to set the assembly onto the retractor by placing the two portions in magnetized or unmagnetized positions.

FIG. 15C illustrates a threaded type support which can easily be set using conventional tooling. FIG. 15D illustrates a spring loaded ball bearing type support adjustable in a locked or unlocked position depending on the lateral position of the balls. The figure illustrates the locked mode, in which the balls are projected and maintained in a locking arrangement by cooperating with a grooved portion of the retractor. In the unlocked position, the groove is free and the support can be removed. FIG. 15E illustrates a hydraulic deployment arrangement A set screw acts on a piston arrangement which can cause a lateral flexible membrane expansion or retraction under the effect of an inner oil pressure increase or decrease respectively. FIG. 15F illustrates a mechanical wedge type support.

The above variants are only examples of attachment means that could be provided. Other types of variants may be used, without departing from the spirit of the invention.

According to the invention, the positioning means could be positioned at least in six different orientations with respect to the sternum retractor, and consequently the patient's heart (see FIGS. 13A to 13E illustrating examples of rail configuration): four orientations along the perimeter of the retracted chest cavity, and two cross-corner diagonal orientations. This maximizes the options for optimum accessibility to the target artery. Of course, according to the respective longitudinal position of the articulations along the arms, a plurality of other positions is also possible. Furthermore, if two rails are used, the possibilities will still be increased.

FIG. 16 shows a variant with easy to connect/disconnect positioning means. Such a variant could be used with any embodiment, with or without rails. A resilient dip assembly 300 of known type could be provided. Such an arrangement enables the surgeon to place the contacting means with more flexibility and allows an easier access to the working volume, which is in general a small volume, difficult to access as many complex instruments obstruct the cavity. This embodiment allows easy access without having to proceed to many adjustments; these adjustments are advantageously performed after the contacting means are well placed. The figure also illustrates an example of rod type rails on which an annular articulation can be slidingly placed. The quick assembly/disassembly function can also be achieved via variety of interfaces (cam-type locking devices, toggle devices, screw type devices, mechanical magnets, etc.).

Figure 17:
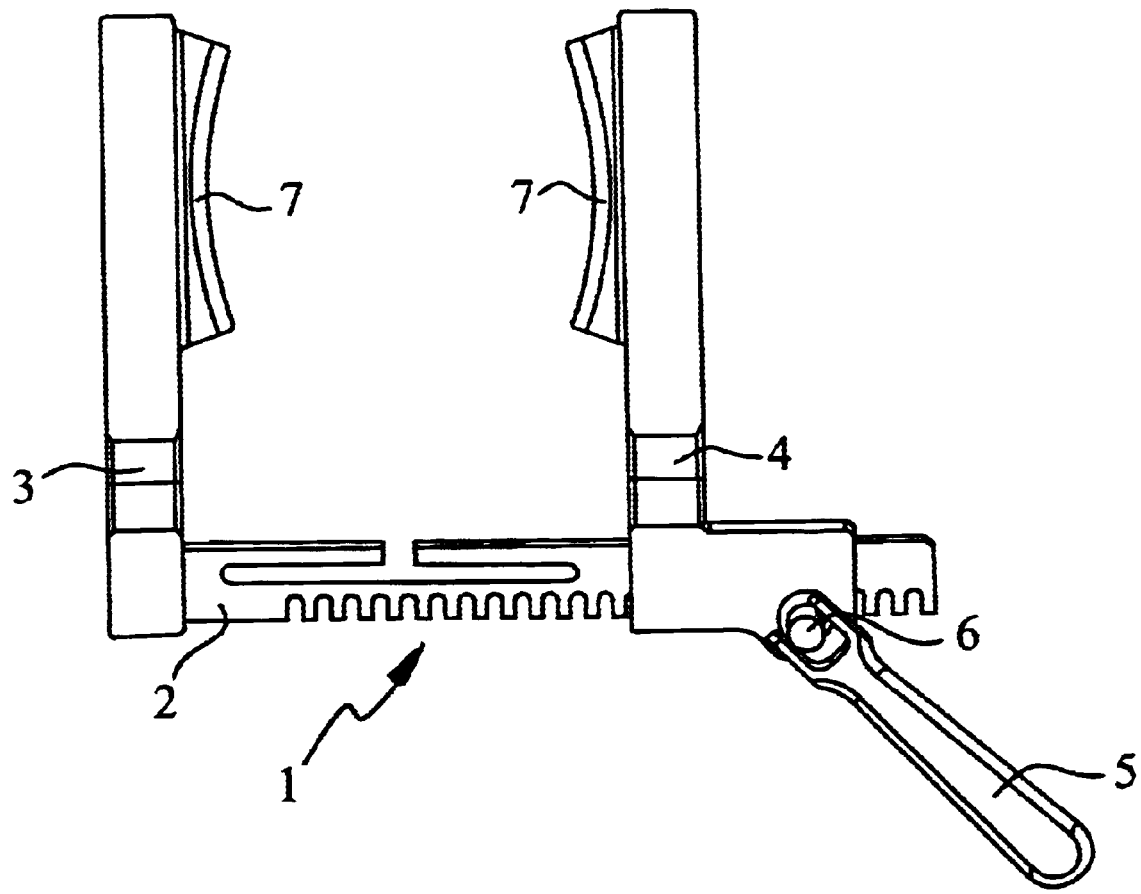
FIG. 17 is a fragmentary top view of a sternum retractor according to the invention.

FIG. 17 shows a variant in which the positioning means, and namely the articulation member, are attached to the sternum retractor via a slot provided on the rack bar. Such a slot can be realized on an existing retractor, resulting in a retrofit arrangement. It can also be provided on a retractor specifically as per the invention.

Figure 18A:
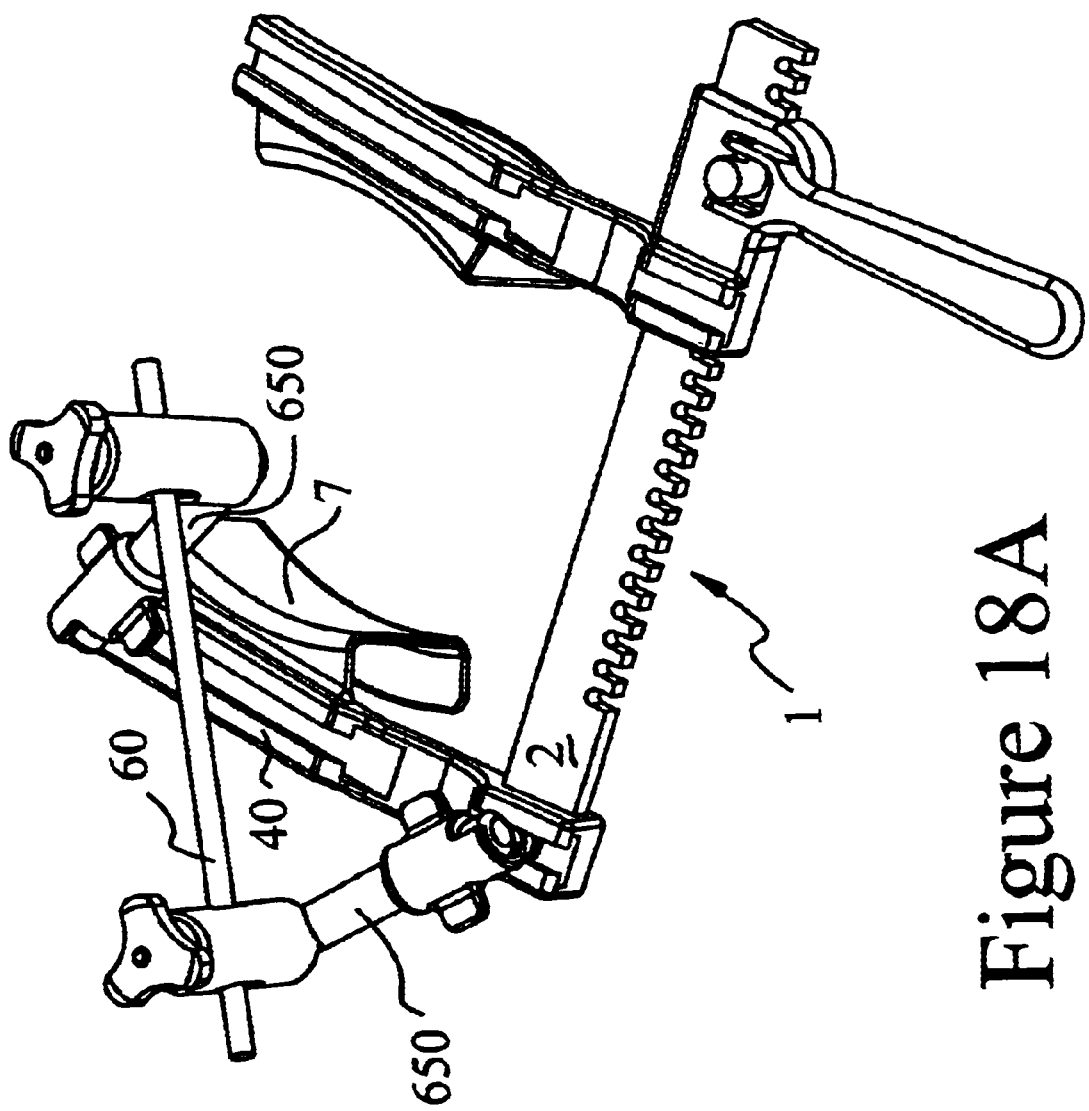
FIGS. 18A to 18C are examples of variants of the embodiment described in FIG. 5A.
Figure 18B:
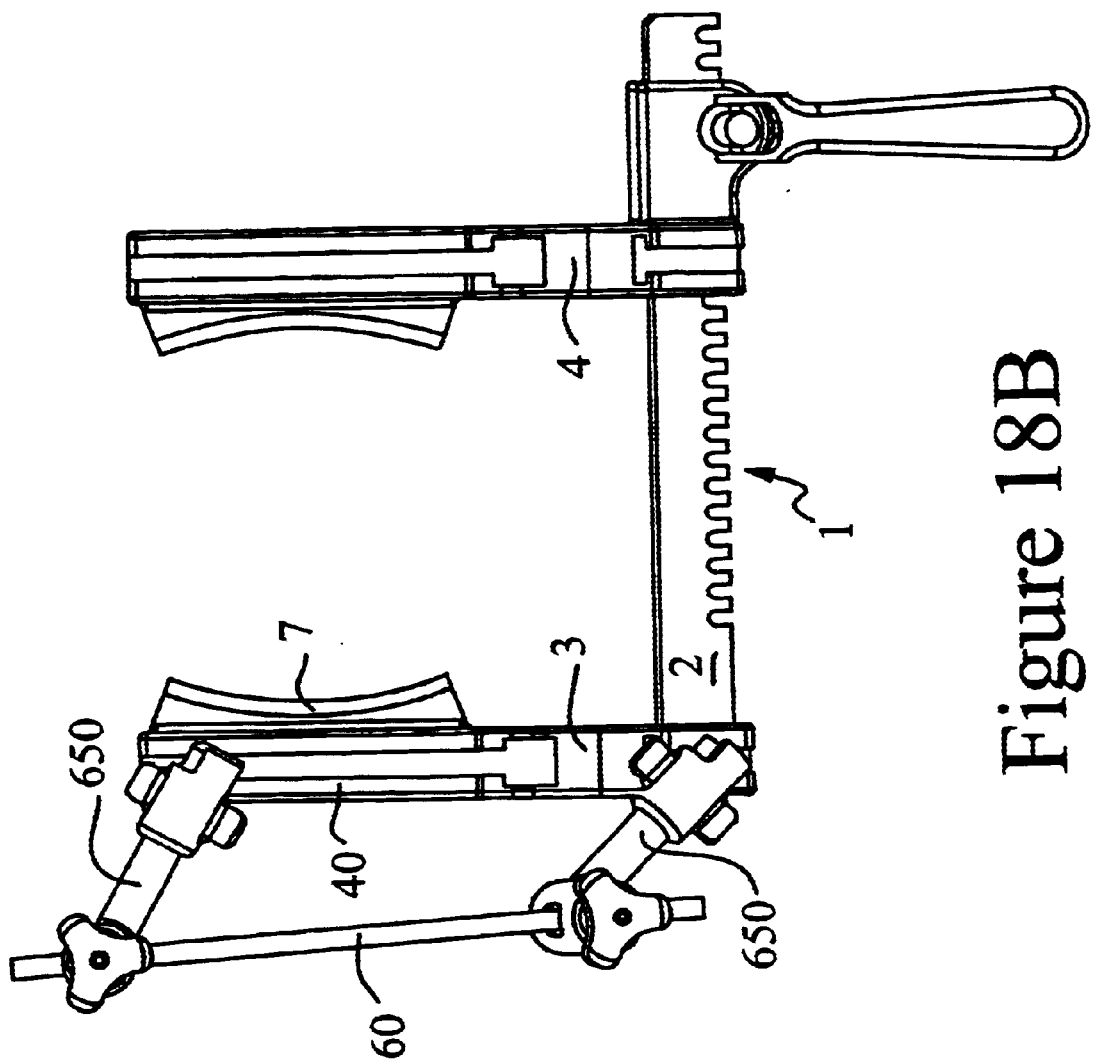
Figure 18C:
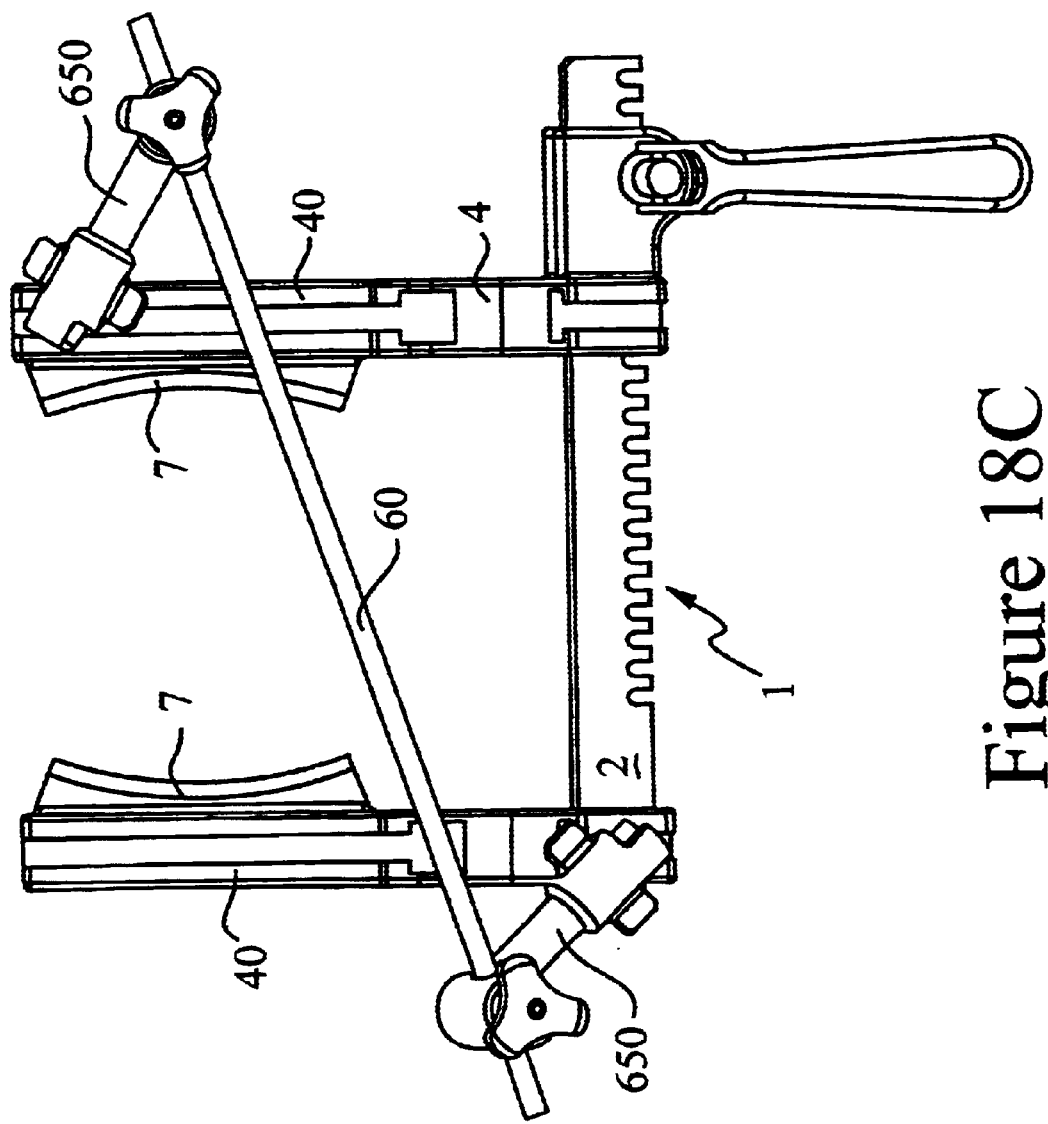

FIGS. 18A to 18C ilustrate a variant where the articulation members 650 are bent in such a way to place the rod member 60 laterally distant from the sternum retractor 1. With such an arrangement, the working area is of easy access and with enhanced ergonomy.

Figure 19:
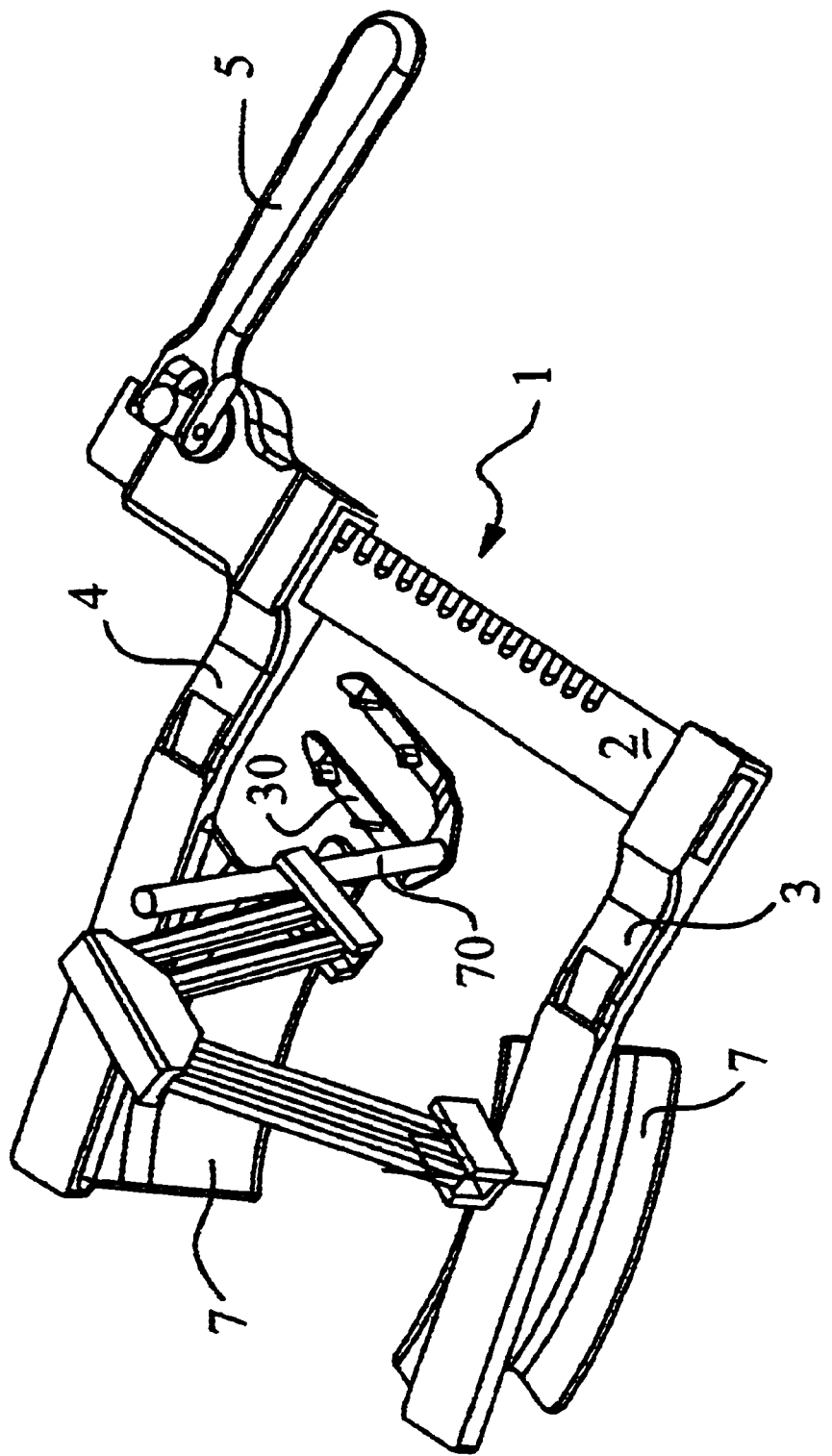
FIGS. 19 and 20 illustrate variants of the embodiment of FIG. 1A.
Figure 20:
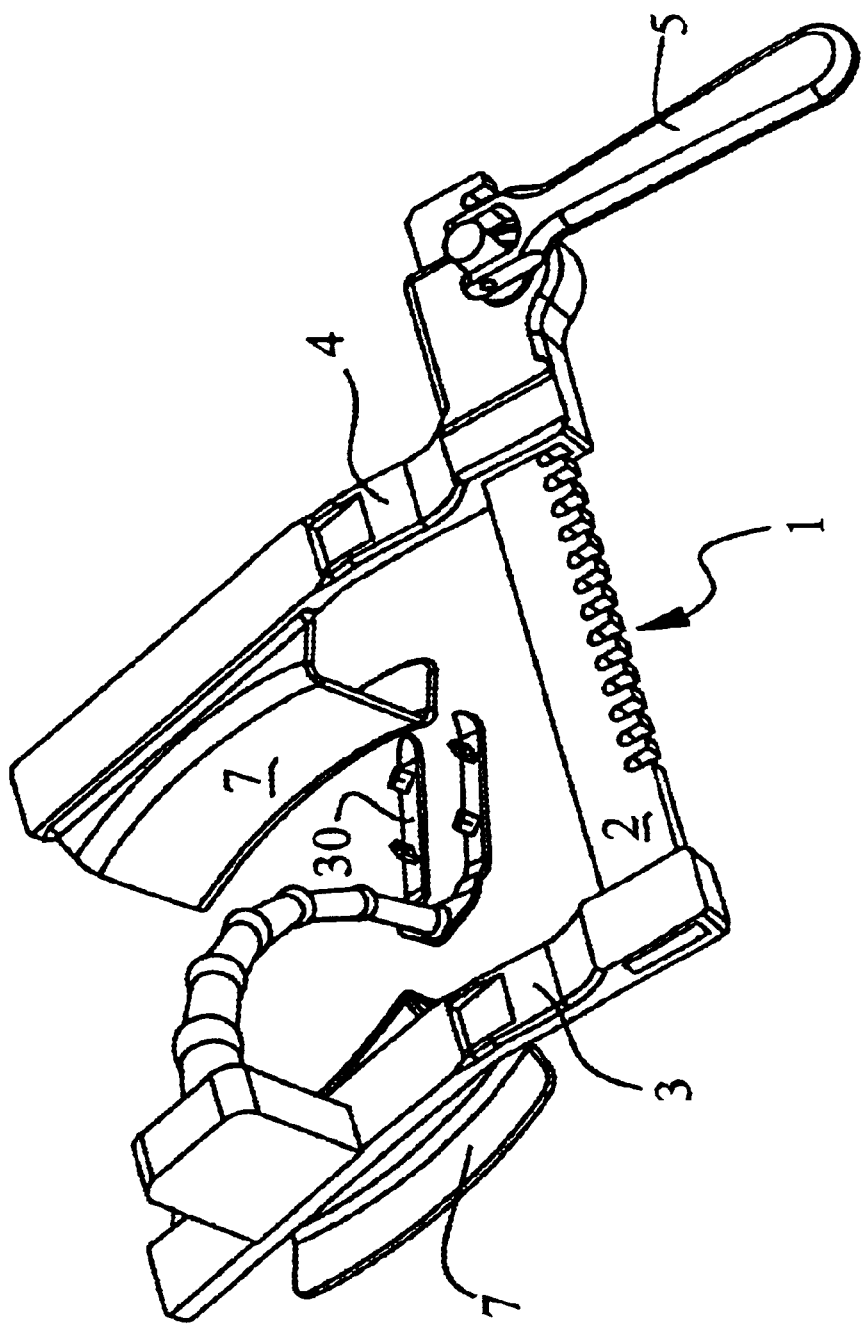
Figure 21A:
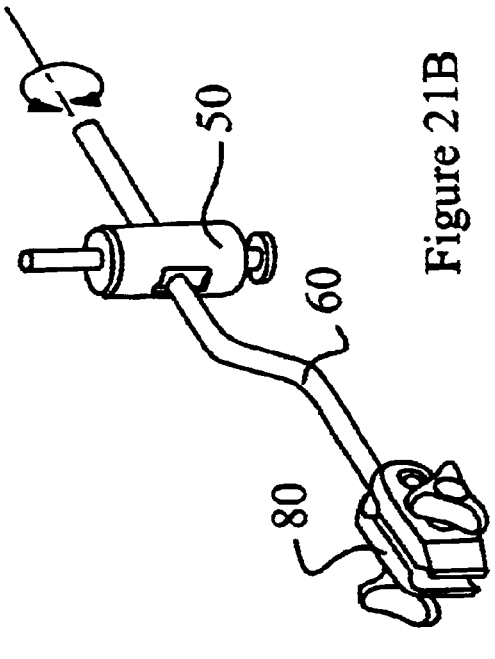
FIGS. 21A to 21D illustrate further variants of the embodiment of FIG. 1.
Figure 21B:
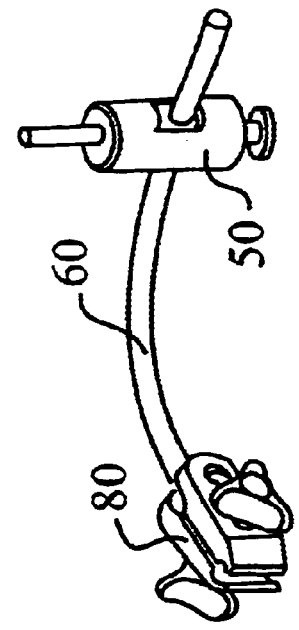
Figure 21C:
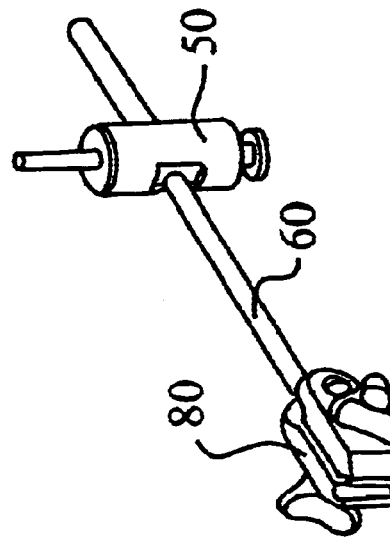
Figure 21D:
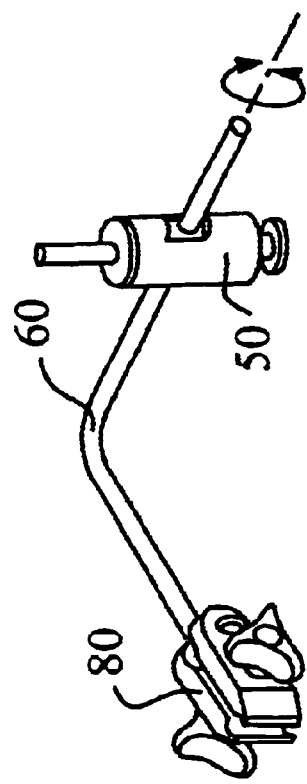

FIGS. 19 and 20 show variants of the embodiment previously described and illustrated in FIG. 1A The articulation members and rods of the embodiment of FIG. 1A are replaced by known-type arms capable of providing rotation, pivoting and translational motions or the like. These arms types are similar to those encountered in desk lamps. These variants are advantageously simple to manufacture, quick and easy to adjust. Other variants offering similarities to these ones can also be provided, sometimes with less positioning capabilities, for example without rotation, without pivoting movement, etc.

FIGS. 21A to 21D illustrate variants of shapes for the positioning rods. Shapes in a straight line, curved, elbowed or double elbowed, etc. These are only examples of an almost unlimited type of shapes that can be used without departing from the spirit of the invention.

Figure 22B:
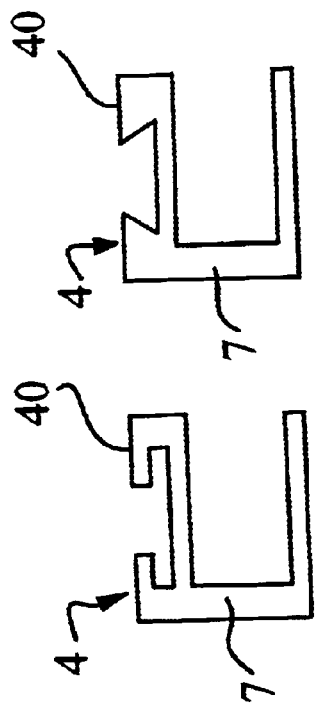
FIGS. 22B–22F illustrate examples of rail profiles used on a sternum retractor illustrated in FIG. 22A.
Figure 22C:
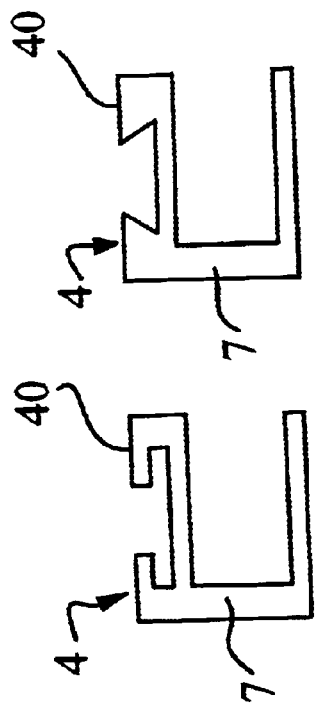
Figure 22A:
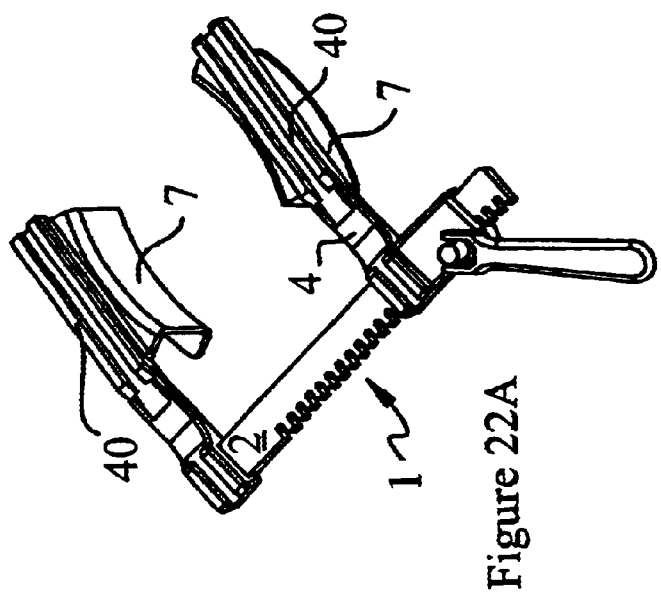
FIG. 22A is a perspective view of a sternum retractor illustrated in FIG. 1A.
Figure 22D:
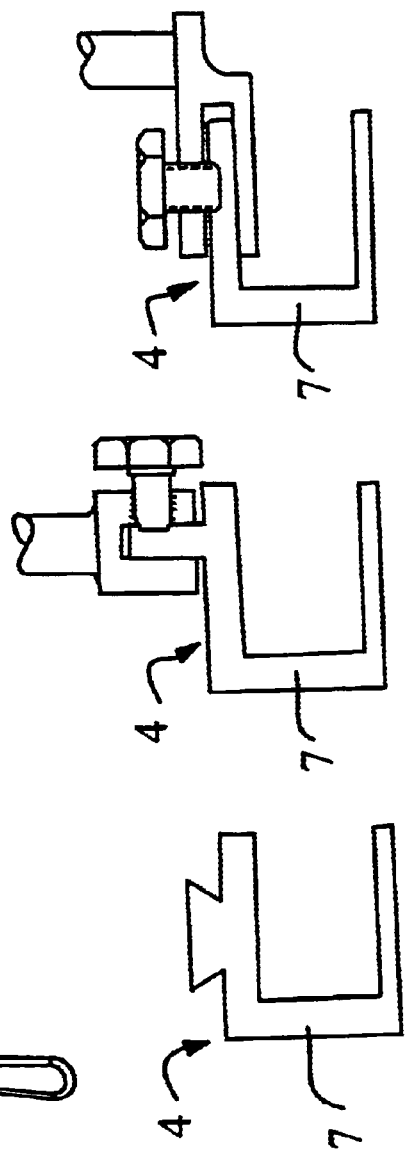
Figure 22E:
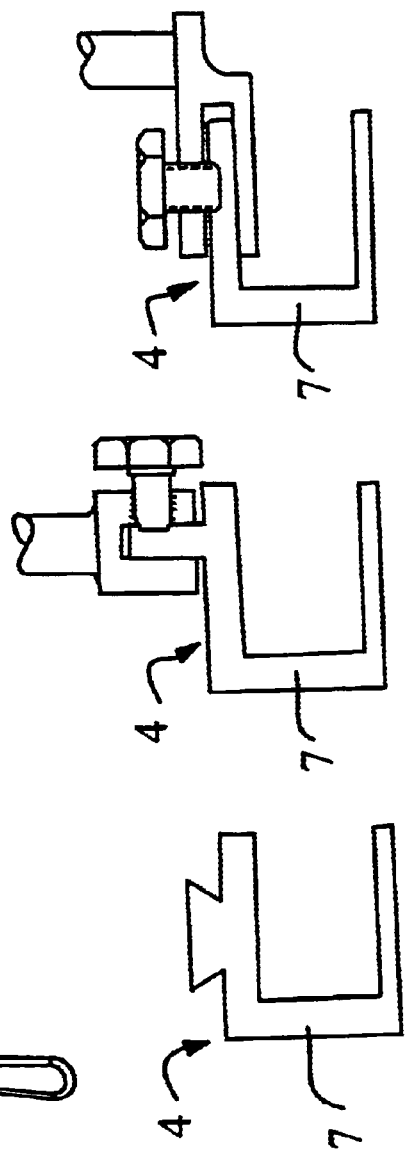
Figure 22F:
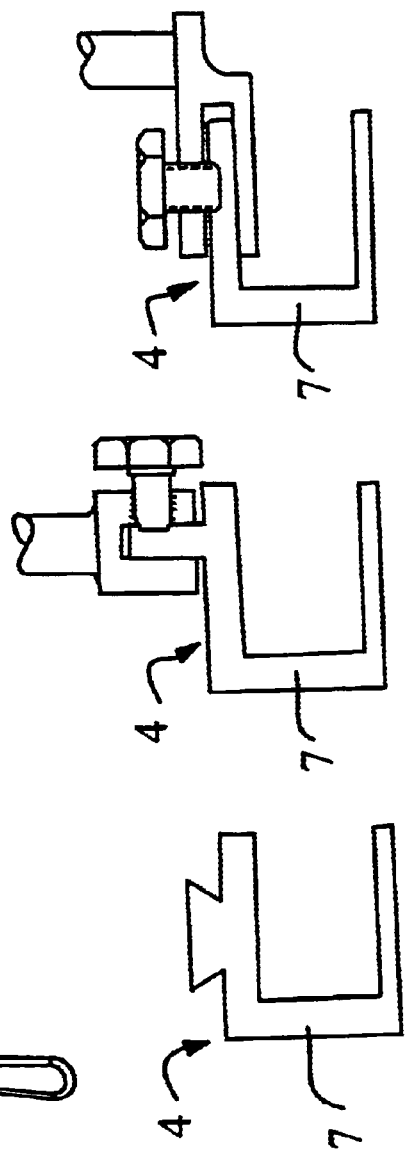

FIGS. 22A and 22F illustrate examples of different shapes of rails that can be used to provide the sliding movement of the positioning means: rectangular, dovetail, etc. These are only examples of an almost unlimited type of shapes that can be used without departing from the spirit of the invention.

Figure 23A:
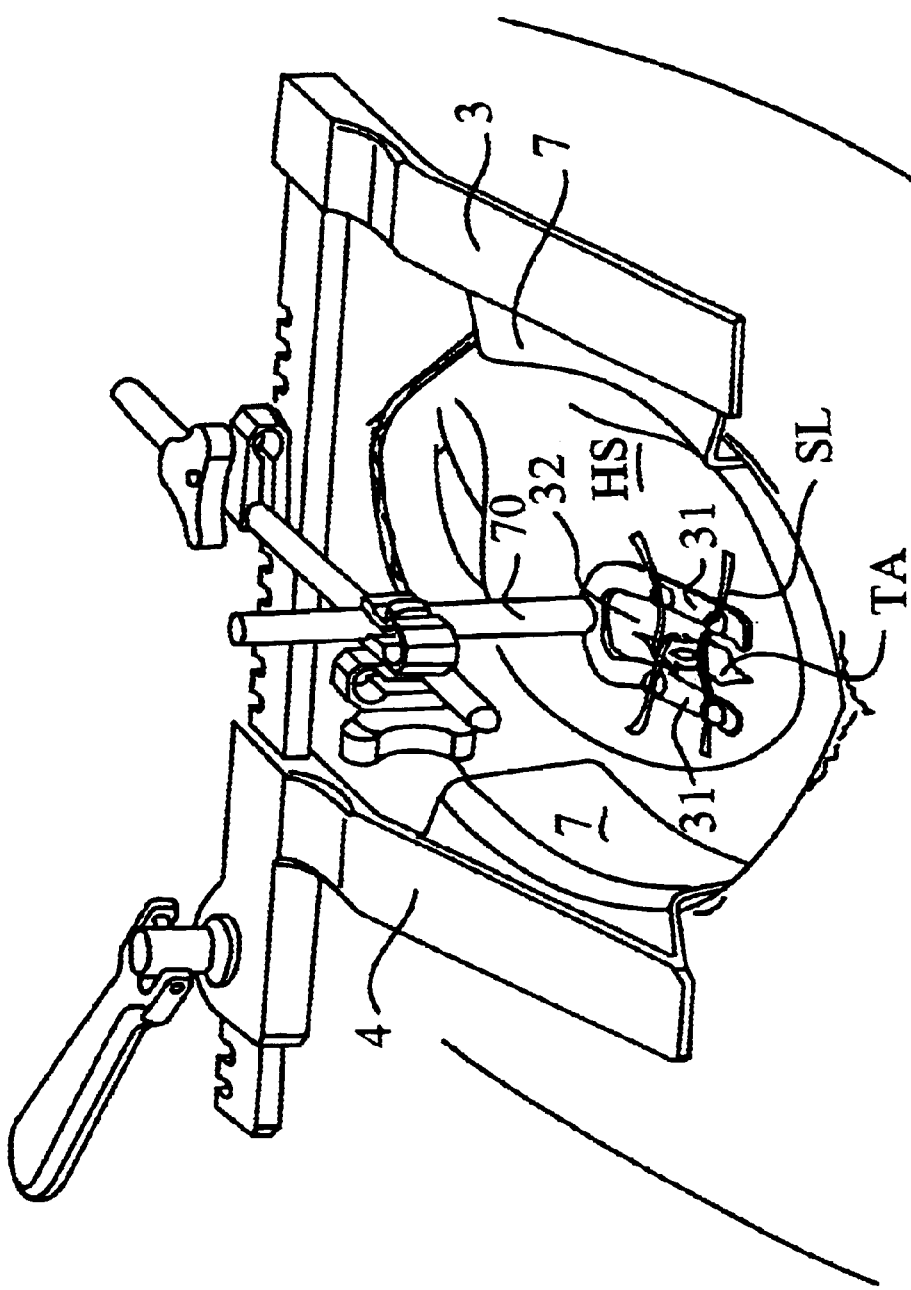
FIGS. 23A and 23B illustrate perspective views of the surgical apparatus according to the invention, in use during a coronary artery revascularization.
Figure 23B:
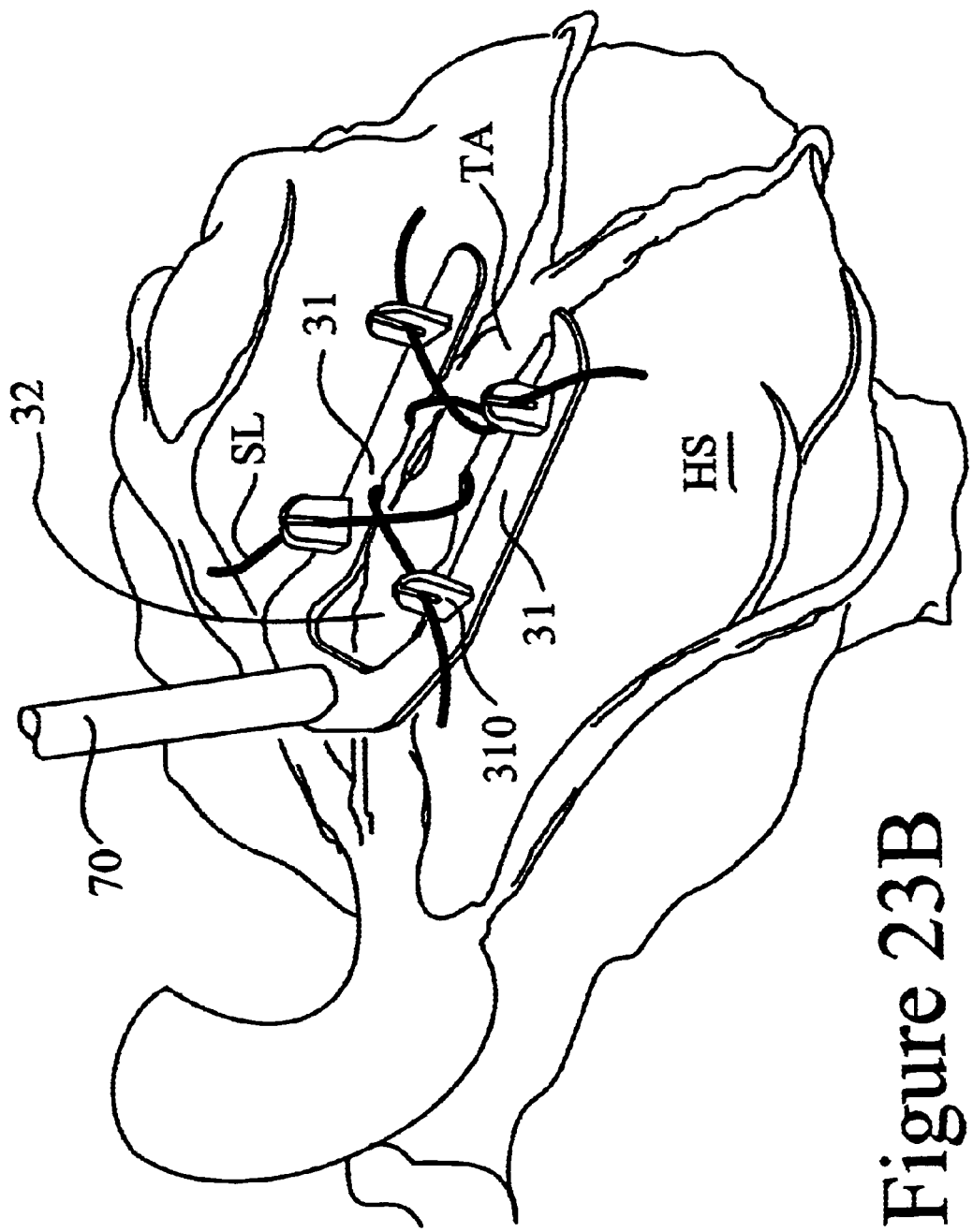

FIGS. 23A and 23B illustrate the contacting means 30 when placed against the heart surface. Two elongated contacting arms 31 defining therebetween an arterial window 32 are provided. The two arms are preferably substantially parallel and the slot defined by their inner edge is used as an arterial window. That is to say that the target artery TA will be aligned between these two arms when the contacting means is adequately placed. The arms are shaped to be capable to press against the heart surface HS immediately surrounding the target artery. In this way, the target artery becomes easily accessible for the surgery purpose. As a result, the heart stabilizer locally prevents the heart from moving around the target artery, allowing thus direct coronary bypass surgery on a beating heart. In areas where the arteries are incrusted in the heart surface, the contacting arms provide a way to raise the target artery through the arterial window, thereby increasing access for the purpose of the surgery.

This aspect of the invention can be clearly seen in FIG. 23B. The target artery TA is engaged between the arms 31. The surgeon can thus advantageously attach the Silastic™ wire SL to the portions of the target artery that are upstream and downstream of the grafting site. This provides a very efficient way of restricting the blood flow. The surgeon can then cut the artery and realize the grafting process. Attachment means 310 are preferably provided on the non-contacting surface side in order to set the Silastic™ wire in an optimum position. For example, slotted walls can be provided on the contacting arms 31. These attachment means 310 are spaced sufficiently apart on said contacting arms to allow the grafting process. These attachment means can eventually be adjustable, for example axially with lard to the arms and/or angularly.

Figure 30E:
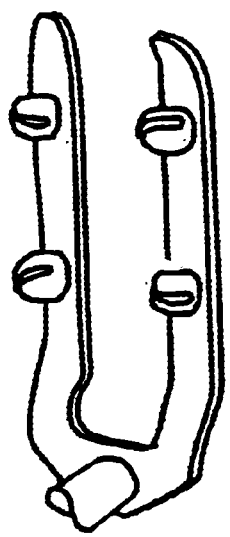
FIGS. 30A to 30G illustrate variants of contacting means provided with different types of attachment means.
Figure 30F:
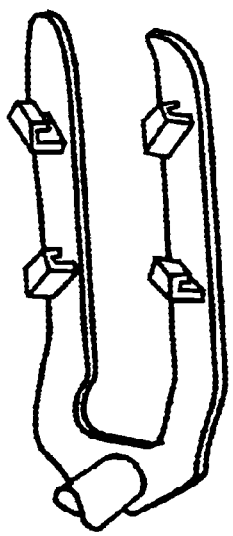
Figure 30G:
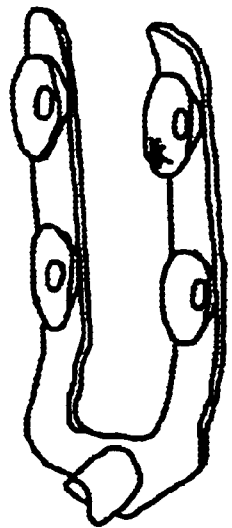
Figure 30B:
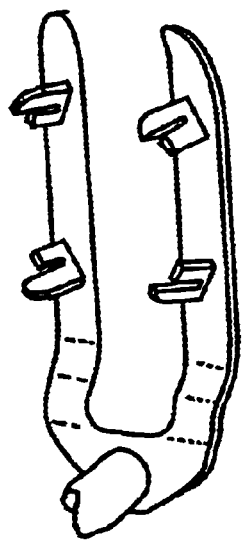
Figure 30C:
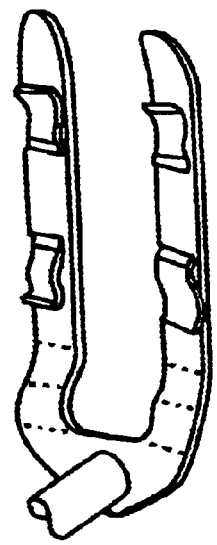
Figure 30D:
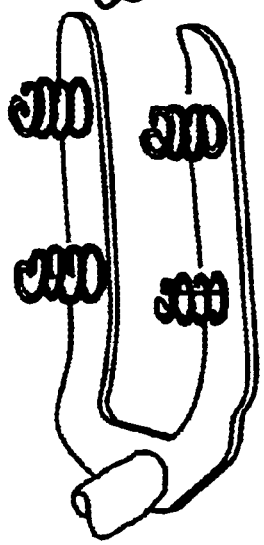
Figure 30A:
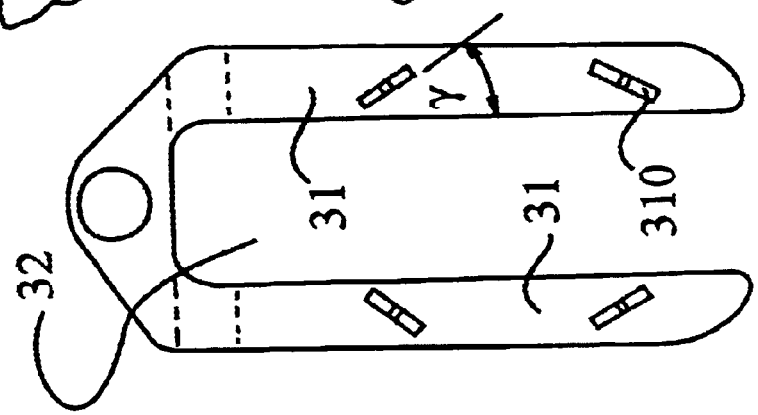
Figures 31A, 31B, 31C, 31D, 31E, 31F:
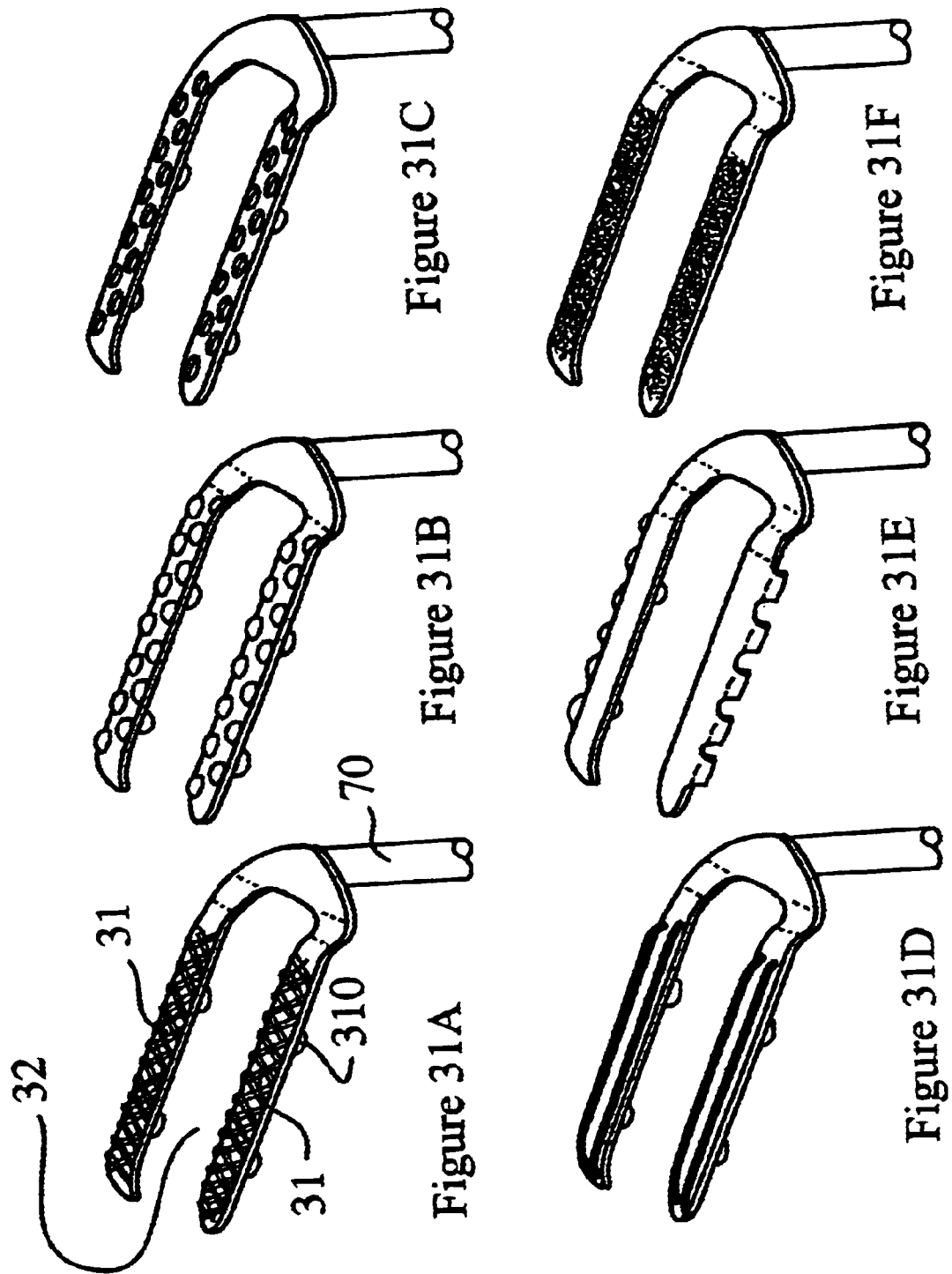
FIGS. 31A to 31F illustrate variants of contacting means provided with different types of textures.

The angle of the attachment means 310 with respect to the contact arm 31 can be determined to coincide with the angle of the Silastic™ wire with respect to said arm as it wraps around the target artery. Furthermore, the walls or the like are preferably capable of being oriented so that the wire penetrates in a substantially normal direction with regard to the walls plane, that is to say a preferred angle γ (see FIG. 30A) between 25 and 80 degrees.

FIGS. 30B to 30G illustrate variants provided with attachment means 310 of different profiles and shapes, respectively "slotted blade type", "clip type", "spring type", "slotted hemisphere type", "hanger type", and "plate-like type". These examples clearly illustrate that the Silastic™, siliconed rubber, silicone elastomer or elastic wire (or other type of wire) can be attached by a plurality of attachment means types.

In order to facilitate the surgery, it is preferable to first set the contacting means against the heart surface in the required position to free the target artery and secondly to secure the contacting means and positioning means assembly to the sternum retractor. To remove the assembly, it is preferable to first disengage the contacting means from the positioning means, thereby easing the separation of the contacting means from the heart surface and minimizing the risk of damage to the newly sutured bypass vessel. Otherwise, the positioning means could also be disengaged first form the retractor, to allow easy separation of the contacting means from the heart surface. In all embodiments, open ended articulation means and/or clamps for the second positioning rod help achieve this quickly and effectively (see FIG. 16).

The profile characteristics of the contacting means are very important. For example, as shown in FIG. 23B, the ending portion of the arms 31 is preferably curved. The arms are advantageously provided with a ski-like shape with the tip portion oriented to be away from the heart surface to prevent damage during involuntary contact, avoiding trauma to the heart surface.

Figure 24:
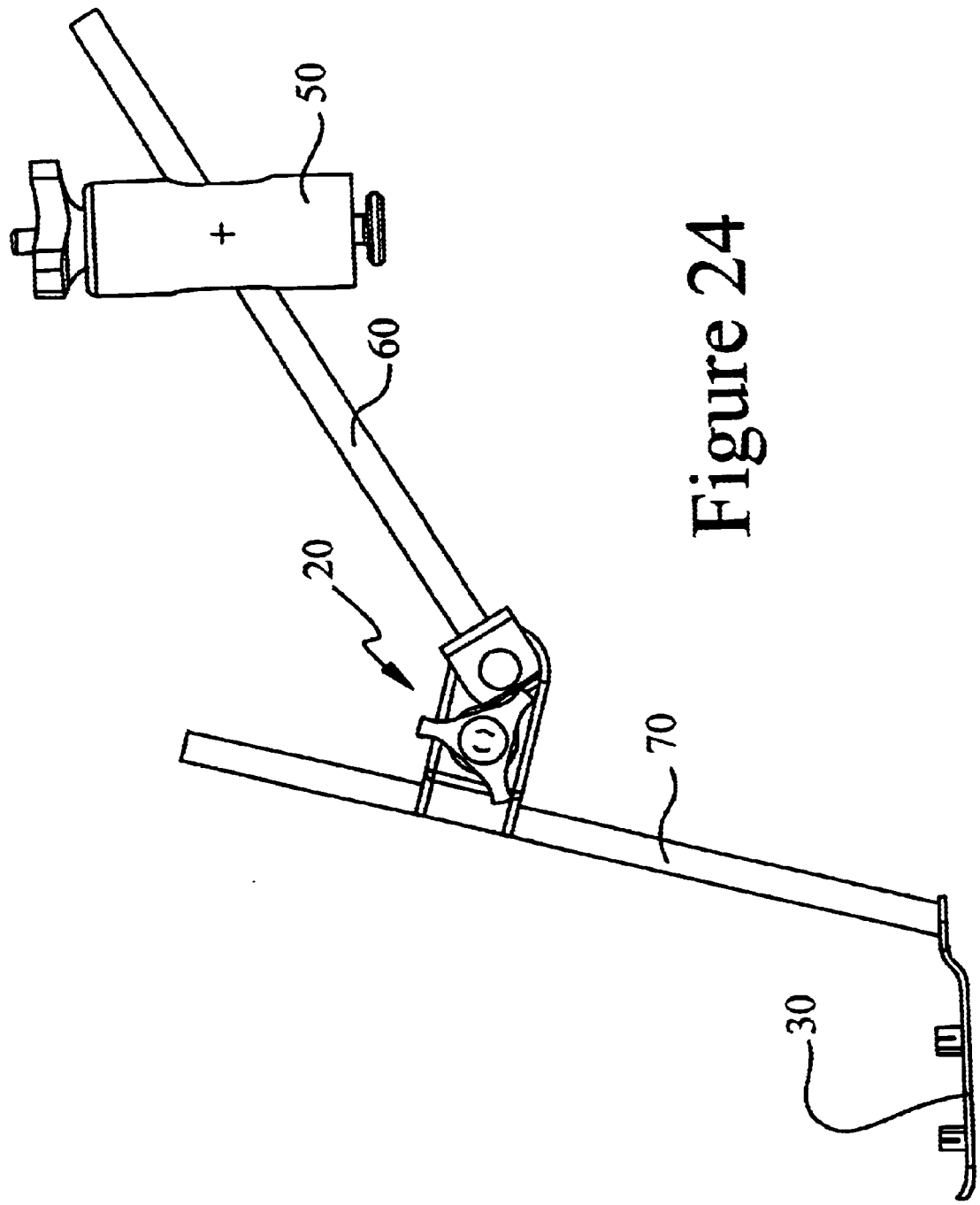
FIG. 24 illustrates a push type configuration according to the invention.
Figure 25:
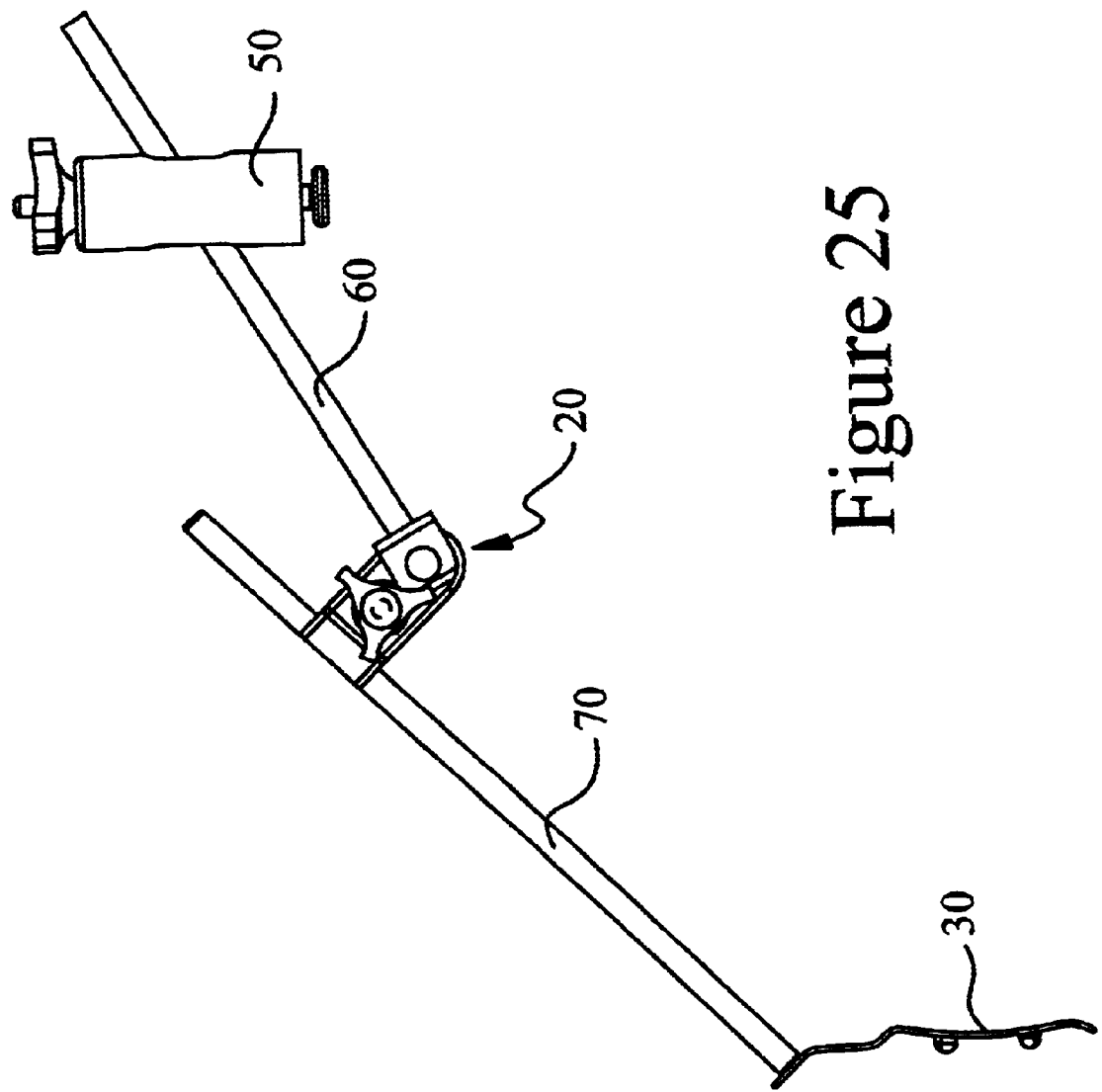
FIG. 25 illustrates a pull type configuration according to the invention.

FIGS. 24 and 25 illustrate two "families" of contacting means. These families originate from the position of the contacting means with regard to the heart during the surgery and/or the type of force resulting from this position. FIG. 24 shows a "push type" arrangement, whereas FIG. 25 shows a "pull type" arrangement. From these figures, it can easily be seen that the positioning means plus contacting means assembly provides respectively a pushing force (see also FIGS. 23A and 23B) and a pulling force (see also FIG. 6). The "push type" and "pull type" are prefered for use with the anterior and posterior arteries respectively. In all embodiments, the motion degrees of freedom of the second articulation means provide the adaptability to cater for push and pull arrangements in a manner to maximize ergonomics of surgery (FIGS. 24 and 25).

The contacting means profile is preferably adapted in function of these two families. FIGS. 26, 27 and 28 show examples of "push type" profiles. The attachment means 310 are then provided on the upper portion of the arms 31. The illustrated example in FIG. 26 is advantageously of oval shape. This facilitates the access to certain arteries that would otherwise be difficult to reach.

Many other profiles are advantageously provided, each one of them matching with a specific area of the heart. FIGS. 27 and 28 illustrate further examples with spoon-like profiles: FIG. 27 with standard spoon configuration (convex contact) and FIG. 28 with concave contact. Adapted profiles are preferable for maximum surface coverage, thereby minimizing heart trauma. Moreover, the interface surface with the beating heart is optimized to maximize stability while minimizing risk of damage to the heart.

Figure 29:
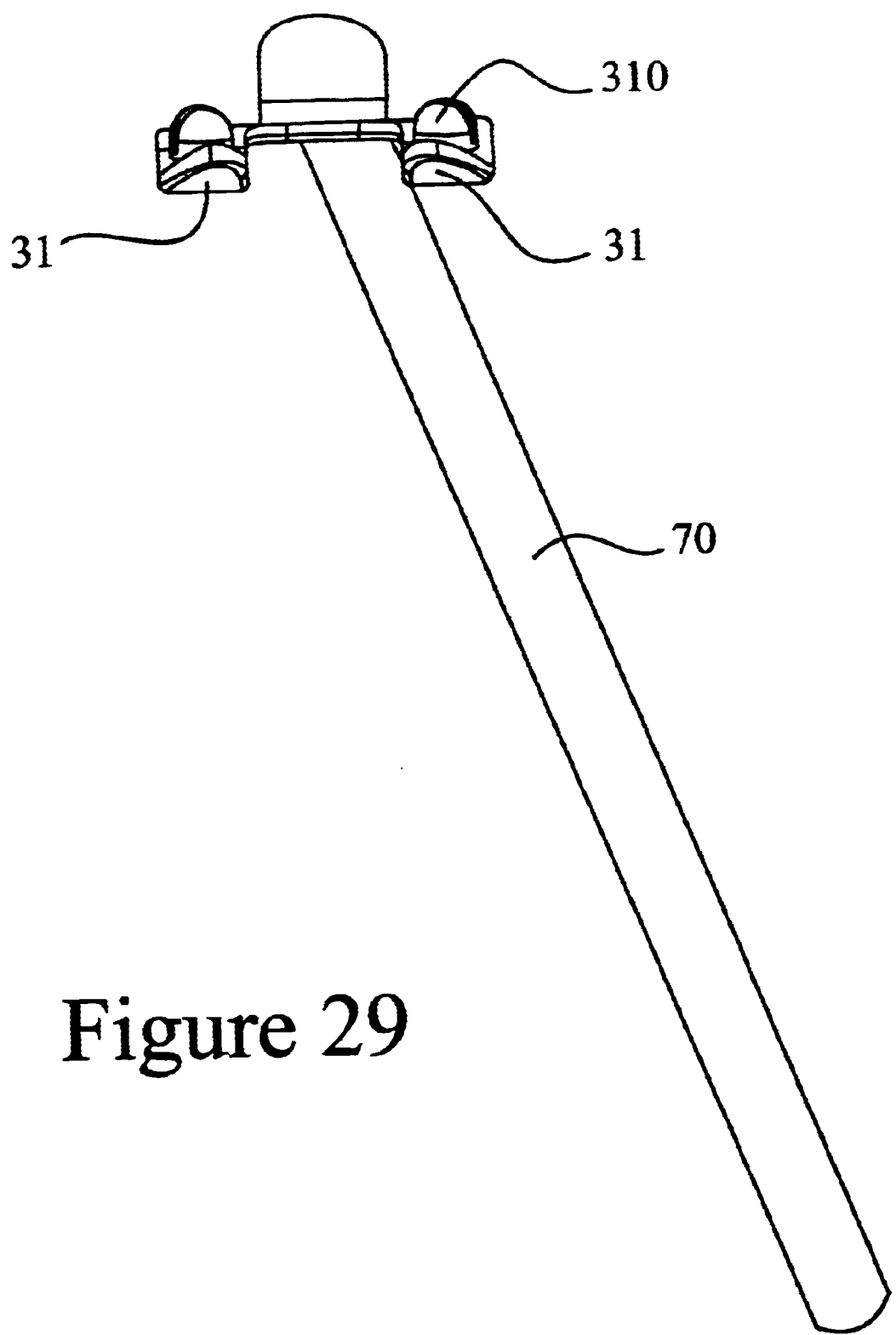

FIGS. 29A and 29B show a variant of "pull type" arrangement, in which a given angle is provided between the positioning rod and the contacting means.

FIGS. 31A to 31F show variants of the contacting means with textured surfaces favoring adherence between the arms 31 and the heart surface, to ensure minimum slip with regard to the heart tissue for example caused by the heart pulsation. Various types of textures can be provided, like for example, (from FIGS. 31A to 31F respectively) with grooves, with dimples/pedestals, with holes, with perimeter fence, with jagged outer contour, with covalently bonded surface treatment, etc. This helps to prevent "skidding" or "slipping" on either side of target artery during grafting. The contacting means are provided to be in relation with the cardiac organs, in particular the heart. The terms "cardiac organs" comprise the heart, but also the surrounding vessels and tissues, in particular the mediastinum, the pericardium, the thymus; the area between two lungs, etc.

To simplify the surgeon's task and to free the cavity for better ergonomics, the positioning rods may also provide different features, like holes or grooves, or the like.

Figure 32:
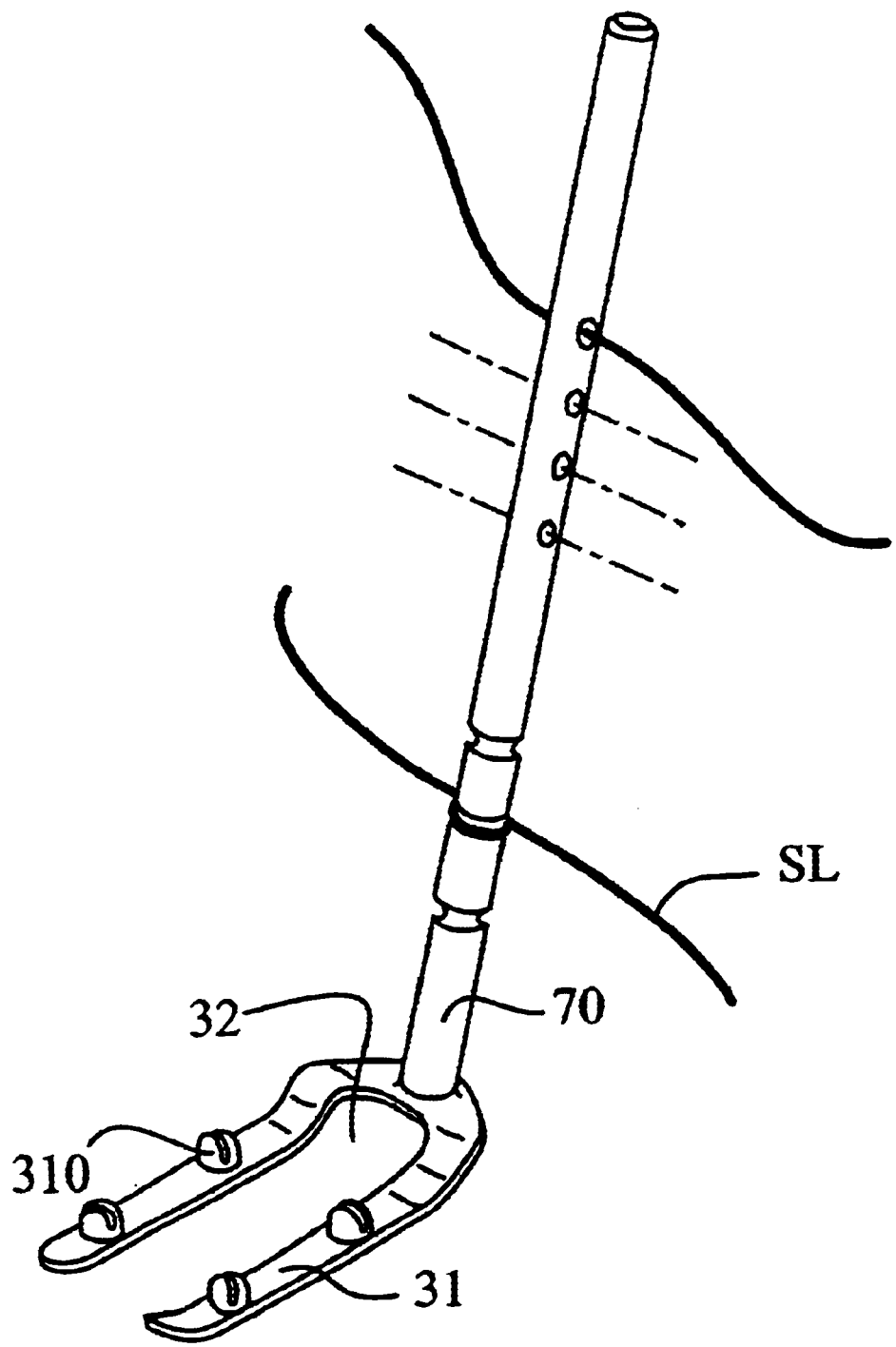
FIG. 32 illustrates a variant of a positioning rod.

FIG. 32 illustrates an example in which grooves and holes are used as anchoring points. Those features can also be used with Silastic™ wire, suturing wire, suturing silk, silicon loops or the like inserted through said holes and/or said grooves, and attached to anchoring means on the sternum retractor to brace and maintain the assembly as rigidly as possible.

The different parts and components of the present invention can be manufactured from either a biocompatible plastic, for example medical grade ABS, for single use, or in surgical stainless steel or any other biocompatible sterilizable material to allow for repeat usage.

The above description of the preferred embodiments should not be interpreted in any limiting manner since variations and refinements are possible without departing from the spirit of the invention.

We claim:

1. An articulation member for use in a surgical apparatus used with a surgical tool having an arm, said articulation member being mountable on a support structure, said articulation member comprising:

a fitting for mounting to said support structure;

a socket coupled to said fitting for receiving said arm of said surgical tool; and a clamp moveable between a loosened position and a tightened position wherein respectively;

in said loosened position said clamp permits translation between said fitting and said support structure along a first translation axis, permits rotation of said fitting relative to said support structure a first rotational axis angled relative to said first translation axis, and permits rotation of said socket relative to said fitting; and in said tightened position, said clamp secures said fitting and said arm relative to said support structure.

2. The articulation member of claim 1, wherein said first rotational axis is angled substantially orthogonal relative to said first translation axis.

3. The articulation member of claim 2, wherein in said loosened position of said clamp, said clamp pennits rotation of said socket relative to said fitting about a second rotational axis, said second rotational axis angled substantially orthogonal relative to said first rotational axis.

4. The articulation member of claim 3, wherein in said loosened position of said clamp, said socket permits translation of said arm through said socket.

5. The articulation member of claim 4, wherein in said loosened position of said clamp, said socket permits rotation of said arm about a longitudinal axis of said arm.

6. An articulation member for mounting on a seat of a surgical support structure, said articulation member being usable with a surgical tool having an arm, said articulation member comprising:

a body;

a footing extending from said body, said footing being configured and sized so as to be engageable with said seat;

a socket mounted to said body for receiving said arm of said surgical tool; and a clamp mounted to said body and moveable between a tightened condition and a loosened condition wherein respectively;

in said loosed condition of said clamp, said footing is translatable relative to said seat along a first translational axis, said body is rotatable relative to said seat about a first rotational axis angled relative to said first translational axis, and said socket is rotatable relative to said body; and in said tightened condition said clamp binds said footing to said seat and secures said socket relative to said body.

7. The articulation member of claim 6, wherein in said loosened condition of said clamp, said socket permits translation of said arm through said socket, and in said tightened condition said clamp holding said arm relative to said socket.

8. The articulation member of claim 7, wherein in said loosened condition of said clamp, said socket permits rotation of the arm about a longitudinal axis of said arm.

9. The articulation member of claim 7, wherein in said loosened condition of said clamp, said socket is rotatable relative to said body about a second rotational axis angled relative to said first rotational axis, and in said tightened condition said clamp secures said body relative to said seat.

10. The articulation member of claim 9; wherein in said loosened condition of said clamp, said arm pivots about said second rotational axis.

11. The articulation member of claim 9, wherein said first rotational axis is angled substantially orthogonal to said first translational axis, and said second rotational axis is angled substantially orthogonal to said first rotational axis.

12. The articulation member of claim 7, wherein said socket has a first portion and a second portion, each of said portions having opposed inner profiles, and said articulation member is operable to urge said first portion towards said second portion to engage a tool arm therebetween.

13. The articulation member of claim 7, wherein:

said body having a bore defined therein;

said clamp being housed within said bore and having a pair of tension members with opposed inner concave profiles, said socket being engaged between said opposed inner concave profiles, and said tension members being operable to apply compression to said socket.

14. The articulation member of claim 6, wherein said body has a shoulder for bearing against said support structure, said clamp being operable to force said shoulder against said support structure and said footing against said seat, thereby binding said footing relative to said seat.

15. The articulation member of claim 6, the seat being a track-way having a channel-shaped cross-section and an overhanging flange wherein said clamp is tightenable to draw said footing against a first portion of the flange, and to urge said body against a second generally opposing portion of the flange thereby holding said flange between said footing and said body.

16. The articulation member of claim 6, wherein said surgical support structure is a surgical retractor and said seat is integral with a member comprising said surgical retractor.

17. An articulation member for mounting on a seat of a surgical support structure, said articulation member being usable wit a surgical tool having an arm, said articulation member comprising:

a body;

a footing extending form said body, said footing being configured and sized so as to be engageable with said seat;

an adaptor coupled with said body for receiving said arm of said surgical tool; said adaptor being modifiable so as to allow pivotal movement of said arm relative to said body, and a clamp mounted to said body and moveable between a tightened condition and a loosened condition wherein respectively;

in said loosened condition of said clamp, said footing is translatable relative to said seat along a first axis, said body is rotatable relative to said seat about a second axis angled relative to said first axis, the body rotation about said second axis being independent from said pivotal movement of said arm; and in said tightened condition said clamp binds said footing to the seat and secures orientation of said body relative to said seat.

18. The articulation member of claim 17, wherein in said loosened condition of said clamp, said adaptor is rotatable relative to said body about a third axis angled relative to said second axis, and in said tightened condition said clamp secures orientation of said adaptor to said body.

19. The articulation member of claim 18, wherein said adaptor having a hollow portion, and wherein in said loosened condition of said clamp, said adaptor permits translation of said arm through said adaptor, and in said tightened condition said clamp holds said arm at the adaptor.

20. The articulation member of claim 19, wherein in said loosened condition of said clamp, said adaptor permits rotation of said arm about a longitudinal axis of said arm.

21. The articulation member of claim 20, wherein said adaptor is a split socket comprised of an opposed pair of shells, each of said shells having an inner surface comprising a sector of a right cylindrical surface for engaging a round cylindrical portion of a tool arm, said clamp being operable to tighten said shells on the arm.

22. The articulation member of claim 19, wherein:
said body having a bore defined therein;
said clamp being housed within said bore and has a pair of tension members with opposed inner concave profiles, said adaptor being a socket being engaged between said opposed inner concave profiles, and said tension members being operable to apply compression to said socket.

23. The articulation member of claim 18, wherein said second axis is angled substantially orthogonal to said first axis, and said third axis is angled substantially orthogonal to said second axis.

24. The articulation member of claim 17, wherein in said loosened condition of said clamp, said adaptor permits translation of said arm relative to said adaptor, and in said tightened condition said clamp holds said arm at the adaptor.

25. The articulation member of claim 24, wherein said adaptor has a first portion and a second portion, each of said portions having opposed inner profiles, and said articulation member is operable to urge said first portion towards said second portion to engage a tool arm therebetween.

26. The articulation member of claim 17, wherein said body has a shoulder for bearing against said support structure, said clamp being operable to force said shoulder against said support structure and said footing against said seat, thereby binding said footing relative to said seat.

27. The articulation member of claim 17, wherein said seat being a track-way having a channel-shaped cross-section and an overhanging flange, and wherein said clamp is tightenable to draw said footing against a first portion of the flange, and to urge said body against a second generally opposing portion of the flange thereby holding said flange between said footing and said body.

28. The articulation member of claim 17, wherein said seat including a raised protrusion protruding from said support structure, said raised protrusion configured and sized for complementary engagement with said footing so as to allow slideable movement therebetween in said loosened condition.

29. An articulation member for use in a surgical apparatus usable with a surgical tool having an arm, said arm having a longitudinal axis said articulation member being mountable on a rack bar of a surgical retractor, said rack bar being elongate and defining a longitudinal axis, said articulation member comprising:
a fitting for mounting to said rack bar of said surgical retractor,
an adaptor coupled to said fitting, said adaptor configured and sized for receiving said arm of said surgical tool said adaptor allowing pivotal movement of said arm relative to said fitting; about an axis angled relative to said arm longitudial axis, and
a clamp moveable between a loosened position and a tightened position wherein respectively;
in said loosened position said clamp permits rotation of said fitting relative to said rack bar about a rotational axis angled relative to said longitudinal axis of said rack bar; and
in said tightened position, said clamp secures said arm relative to said rack bar.

30. In combination with a rack bar, an articulation member being mountable on a rack bar of a surgical retractor, said rack bar being provided with with movement means for imparting relative movement between two members of said surgical retractor, said articulation member usable with a surgical tool having an arm, said articulation member comprising:
a body
a footing extending from said body, said footing configured and sized so as to be engageable with a seat on said rack bar;
an adaptor mounted to said body, said adaptor configured and sized for receiving said arm of said surgical tool; and
a clamp mounted to said body and moveable between a tightened condition and a loosened condition wherein respectively;
in said loosened condition of said clamp, said clamp permits rotation of said adaptor relative to said body; and
in said tightened condition said clamp secures said adaptor relative to said body.

31. The articulation member of claim 30, wherein said adaptor having a hollow portion, and wherein in said loosened condition of said clamp, said adaptor permits translation of said arm through said adaptor, and in said tightened condition of clamp said arm is rigidly held relative to said adaptor.

32. The articulation member of claim 31, wherein in said loosened condition of said clamp, said body is rotatable relative to said seat about a first axis relative to said seat, and said arm is pivotable about a second axis angled relative to said first axis, and in said tightened condition said clamp secures said body relative to said seat.

33. The articulation member of claim 32, wherein in said loosened condition of said clamp, said adaptor permits rotation of said arm about a longitudinal axis of said arm.

34. The articulation member of claim 33, wherein said hollow portion of said adaptor is comprised of opposing sectors of a right cylindrical surface for engaging a round cylindrical portion of said tool arm, said clamp being operable to tighten said opposing sectors on said arm.

35. The articulation member of claim 32, wherein said second axis is angled substantially orthogonal to said first axis.

36. The articulation member of claim 31, wherein said adaptor is split, and wherein said hollow portion including a first portion and a second portion, each of said first and second portions having opposed inner profiles, and said articulation member is operable to urge said first portion towards said second portion to engage said surgical tool arm therebetween.

37. The articulation member of claim 30, wherein said seat is an elongated rail and said footing is formed to engage a longitudinal portion thereof.

38. The articulation member of claim 37, wherein said elongated rail is a track-way having a channel-shaped cross-section and an overhanging flange.

39. The articulation member of claim 37, wherein said elongated rail is an integral portion of said rack bar.

40. The articulation member of claim 37, wherein said elongated rail including a raised protrusion protruding from said rack bar, said raised protrusion configured and sized for complementary engagement with said footing.

41. The articulation member of claim 30, wherein said surgical tool is a tissue stabilizer used to perform coronary artery bypass graft surgery.

42. The articulation member of claim 30, wherein said footing is configured and sized to be translatable relative to said seat, and wherein said footing is modifiable so as to allow binding of said footing to said seat.

43. The articulation member of claim 42, wherein in said loosened condition of said clamp, said footing is translatable relative to said seat, and in said tightened condition said clamp binds said footing to said seat.

44. The articulation member of claim 43, wherein said body has a shoulder for bearing against said rack bar, said clamp being operable to force said shoulder against said rack bar and said footing against said seat, thereby binding said footing relative to said seat.

45. The articulation member of claim 40, further including a footing locking means for releasably locking said footing at a predetermined position along said seat.

46. In combination with a rack bar, an articulation member for use in a surgical apparatus usable with a surgical tool having an arm, said articulation member being mountable on a rack bar of a surgical retractor, said rack bar being usable to impart relative movement between two members of said surgical retractor, said articulation member comprising:

a body a footing extending from said body, said footing configured and sized so as to be translatable relative to a seat on said rack bar;

a ball and socket joint formed between said body and said arm for allowing pivotal relative movement therebetween; and a clamp operatively coupled to said footing, said clamp being moveable between a tightened condition and a loosened condition wherein respectively; in said loosened condition of said clamp, said footing is translatable relative to said seat; and in said tightened condition said clamp binds said footing to said seat.

47. In combination with a rack bar, an articulation member for use in a surgical apparatus usable with a surgical tool having an arm, said articulation member being mountable on a rack bar of a surgical retractor, said rack bar being usable to impart relative movement between two members of said surgical retractor, said articulation member comprising:

a body;

a footing extending from said body, said footing configured and sized so as to be translatable relative to a seat on said rack bar;

a ball and socket joint formed between said body and said arm for allowing pivotal relative movement therebetween; and a clamp operatively coupled to said arm, said clamp being moveable between a tightened condition and a loosened condition wherein respectively;

in said loosened condition said clamp permits pivotal movement between said body and said arm; and in said tightened condition said clamp secures said arm relative to said body.

* * * * *